US012591962B2

(12) United States Patent
Andersen et al.

(10) Patent No.: US 12,591,962 B2
(45) Date of Patent: Mar. 31, 2026

(54) METHOD OF EXAMINING A PARTICULATE SUBSTANCE COMPRISING INORGANIC PARTICLES, COMPRISING DETERMINING AT LEAST ONE BINDER QUALITY ASSOCIATED PROPERTY

(71) Applicant: ParticleTech ApS, Farum (DK)

(72) Inventors: Trine Aabo Andersen, Farum (DK); Tom Olesen, Farum (DK); Rasmus Fjordbak Nielsen, Farum (DK)

(73) Assignee: PARTICLETECH APS, Farum (DK)

( * ) Notice: Subject to any disclaimer, the term of this patent is extended or adjusted under 35 U.S.C. 154(b) by 0 days.

(21) Appl. No.: 19/085,345

(22) Filed: Mar. 20, 2025

(65) Prior Publication Data

US 2025/0299312 A1      Sep. 25, 2025

(30) Foreign Application Priority Data

Mar. 22, 2024     (DK) ........................... PA 2024 30137

(51) Int. Cl.
*G06T 7/00*          (2017.01)
*G01N 33/38*         (2006.01)

(52) U.S. Cl.
CPC ......... *G06T 7/0004* (2013.01); *G01N 33/383* (2013.01)

(58) Field of Classification Search
CPC ........................... G06T 7/0004; G01N 33/383
See application file for complete search history.

(56) References Cited

U.S. PATENT DOCUMENTS

| | | | |
|---|---|---|---|
| 4,868,128 A | 9/1989 | Sommer | |
| 5,966,677 A | 10/1999 | Fiekowsky | |
| 6,626,991 B1 * | 9/2003 | Drochon | C09K 8/473 |
| | | | 106/676 |
| 6,873,725 B2 | 3/2005 | Xu | |
| 7,229,491 B2 | 6/2007 | Davidovits | |

(Continued)

FOREIGN PATENT DOCUMENTS

| | | | | |
|---|---|---|---|---|
| CN | 107942041 A | * | 4/2018 | G01N 3/08 |
| CN | 110376360 A | * | 10/2019 | G01N 11/14 |

(Continued)

OTHER PUBLICATIONS

Takashimizu, Y., Iiyoshi, M. (2016). New parameter of roundness R: circularity corrected by aspect ratio. Progress in Earth and Planetary Sciences 3, 2. https://doi.org/10.1186/s40645-015-0078-x (Year: 2016).*

(Continued)

*Primary Examiner* — Fatemeh Esfandiari Nia
(74) *Attorney, Agent, or Firm* — Boone IP Law

(57) ABSTRACT

A method of examining a particulate substance comprising inorganic binder precursor particles is described. The method of examining comprises determining at least one property associated to a binder quality of the particulate substance comprises. The method comprises providing a sample mixture comprising the portion of the particulate substance and a portion of a fluid substance; performing at least one of scanning procedure, wherein each scanning procedure comprises acquiring at least one image of an image acquisition area; processing the acquired image(s) to obtain at least one processed image of each scanning procedure; and determining said at least one binder quality associated property of at least the portion of the particulate substance.

22 Claims, 6 Drawing Sheets

(56)                 References Cited

U.S. PATENT DOCUMENTS

| | | | |
|---|---|---|---|
| 7,634,129 B2 | 12/2009 | Strom | |
| 8,780,181 B2 | 7/2014 | Olesen | |
| 9,290,416 B1 | 3/2016 | Allouche | |
| 2003/0133111 A1 | 7/2003 | Yamaguchi | |
| 2005/0099626 A1 | 5/2005 | King | |
| 2009/0185714 A1 | 7/2009 | Lindberg | |
| 2010/0326213 A1 | 12/2010 | Davidson | |
| 2016/0061806 A1* | 3/2016 | Reid | C04B 12/005 |
| | | | 250/395 |
| 2016/0209372 A1* | 7/2016 | Ziehl | G01N 29/46 |
| 2018/0037505 A1 | 2/2018 | Zubrod | |
| 2019/0161361 A1 | 5/2019 | Tsunematsu | |
| 2019/0225503 A1 | 7/2019 | Okada | |
| 2020/0096434 A1 | 3/2020 | Deran | |
| 2021/0253474 A1* | 8/2021 | Lake | C03B 19/10 |
| 2023/0264156 A1 | 8/2023 | Pereira | |
| 2023/0295046 A1 | 9/2023 | Benck | |
| 2024/0083068 A1 | 3/2024 | Knop | |
| 2025/0145538 A1* | 5/2025 | Calva, Sr. | C04B 14/06 |

FOREIGN PATENT DOCUMENTS

| | | | | |
|---|---|---|---|---|
| CN | 111242909 A | | 6/2020 | |
| CN | 111595848 A | | 8/2020 | |
| CN | 211978616 U | | 11/2020 | |
| CN | 113985013 A | * | 1/2022 | G01N 33/383 |
| CN | 114082888 A | * | 2/2022 | B22C 7/06 |
| CN | 116217156 A | * | 6/2023 | C04B 28/04 |
| CN | 116749343 A | | 9/2023 | |
| CN | 117659502 A | * | 3/2024 | C08G 18/48 |
| EP | 0644414 A2 | | 8/1994 | |
| GB | 2575656 A | | 7/2018 | |
| IN | 201731020161 A | | 12/2018 | |
| JP | 2008268051 A | | 11/2008 | |
| JP | 2009042228 A | | 2/2009 | |
| KR | 101922831 B1 | * | 11/2018 | G01N 21/25 |
| WO | 2004086503 A1 | | 10/2004 | |
| WO | 2007117987 A2 | | 10/2007 | |
| WO | 2010063293 A1 | | 6/2010 | |
| WO | 2014094790 A1 | | 6/2014 | |
| WO | 2014145983 A1 | | 9/2014 | |
| WO | 2014169921 A1 | | 10/2014 | |
| WO | 2017070748 A1 | | 5/2017 | |
| WO | 2019202123 A1 | | 10/2019 | |
| WO | 2019202124 A1 | | 10/2019 | |
| WO | 2019202129 A1 | | 10/2019 | |
| WO | 2022258715 A1 | | 12/2022 | |
| WO | WO-2024121353 A1 | * | 6/2024 | G01N 21/47 |
| WO | 2025016519 A1 | | 1/2025 | |

OTHER PUBLICATIONS

Fan, Liang, et al. "Hyperspectral imaging features for mortar classification and compressive strength assessment." Construction and Building Materials 251 (2020): 118935. (Year: 2020).*

Shakouri, Sahra. Characterization of Portland Cement Compounds with Hyperspectral Imaging. Diss. Middle East Technical University (Turkey), 2023. (Year: 2023).*

Quiroz-Portillo, D., et al. "Study of the Hydration Mechanism of Portland cement with raman spectroscopy applying CO2 laser radiation." Journal of Spectroscopy 2023.1 (2023): 9911266. (Year: 2023).*

Higl, J., et al. "Detailed in situ ATR-FTIR spectroscopy study of the early stages of CSH formation during hydration of monoclinic C3S." Cement and Concrete Research 142 (2021): 106367. (Year: 2021).*

Li, Zaibo, et al. "Selective dissolution and cementitious property evaluation of converter steel slag." Materials and structures 46.1 (2013): 327-336. (Year: 2013).*

Shirani, Shiva, et al. "4D nanoimaging of early age cement hydration." Nature Communications 14.1 (2023): 2652. (Year: 2023).*

Murtaza, Mobeen, et al. "Novel Expandable Cement System for Prevention of Sustained Casing Pressure and Minimization of Lost Circulation." ACS omega 6.7 (2021): 4950-4957. (Year: 2021).*

Kwek et al.: "Influence of Liquid-to-Solid and Alkaline Activator (Sodium Silicate to Sodium Hydroxide) Ratios on Fresh and Hardened Properties of Alkali-Activated Palm Oil Fuel Ash Geopolymer", Materials, 2001, 14, 4253.

Castillo et al.: "State of the art of geopolymers: A review", De Gruyter, e-Polymers 2022, 22: 108-124.

Moodi et al.: "Evaluation of the optimal process of thermal activation of kaolins", Scientia Iranica A (2011) 18 (4), 906-912.

Bayuaji et al.: A review in geopolymer binder with dry mixing method (geopolymer cement), AIP Conference Proceedings 1887, Sep. 29, 2017.

Klaartje De Weerdt: "Geopolymers—State of the art", SINTEF Building and Infrastructure, COIN Project report 37—2011.

Particle Tech Solutions, "Disrupting Process Optimization in Laboratory and Production". Brochure [online], Archieved by Wayback Machine, Dec. 8, 2022 [retrieved on Jan. 29, 2024].

Particle Tech Solutions, "The Smallest Things make a Big Difference". Brochure[online]. Archieved by Wayback Machine, Jan. 18, 2021 [retrieved on Jan. 29, 2024].

Romero et al.: "Evolution of kaolinite morphology upon exfoliation and dissolution: Evidence for nanoscale layer thinning in metakaolin", Applied Clay Science, Mar. 16, 2022, 10 pages.

Forny et al.: "Wetting, disintegration and dissolution of agglomerated water soluble powders", Elsevier, Science Direct Powder Tech., Aug. 2010.

Malvern Panalytical: Morphology 4 Range. Brochure [online], [retrieved on Jun. 20, 2025].

Xue-Dong et al.: "Characterization of Particle Size Distribution (PSD) Evolution during Floculation by an Image Acquisition and Analysis System" In; 2009 International Conference on Environmental Science and Information Application Technology, IEEE, 2009, p. 362-366. Available online.

* cited by examiner

Source for mining/binder precursor extraction
Classification w. hyperspectral

Optimizing processing of precursor
PSD + reactivity

Quality control of processed precursor
PSD + reactivity

Design and optimization of product properties
Reactivity & effect of curing conditions

On-site product quality testing
Reactivity & prediction of curing process                Fig. 5
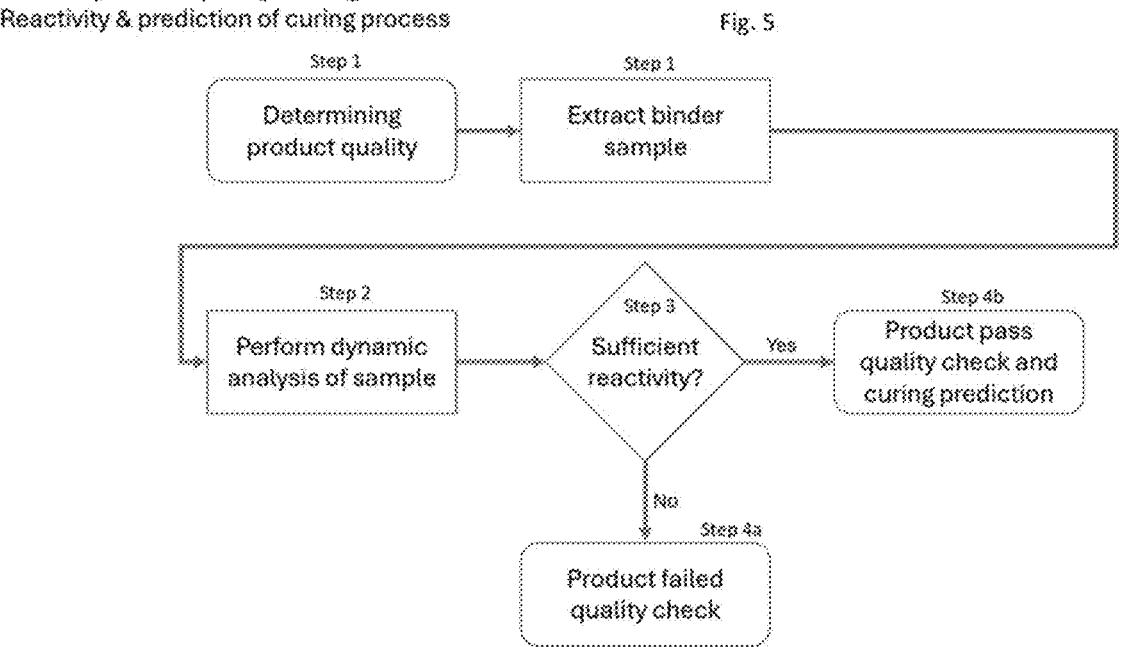
On-site concrete maturity testing
Reactivity & prediction of curing process            Fig. 6
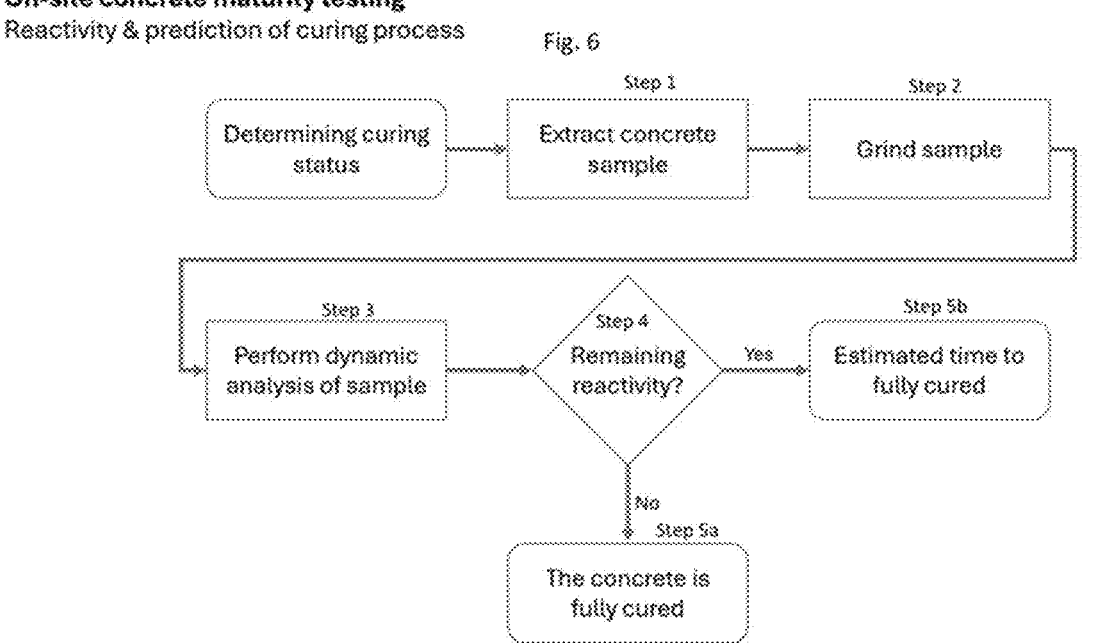

METHOD OF EXAMINING A PARTICULATE SUBSTANCE COMPRISING INORGANIC PARTICLES, COMPRISING DETERMINING AT LEAST ONE BINDER QUALITY ASSOCIATED PROPERTY

TECHNICAL FIELD

The invention relates to a method for determining at least one property associated to a binder quality of a particulate substance comprising inorganic binder precursor particles

BACKGROUND ART

Inorganic binders have played a crucial role in various industries, including construction, ceramics, and metallurgy, among others. Their development has been driven by the need for materials with specific properties such as strength, durability, and resistance to environmental factors.

Lime and gypsum have been used as inorganic binders for thousands of years. Lime, derived from limestone, has been utilized in mortar and plaster applications, while gypsum, obtained from gypsum rock, has been employed in plaster and cementitious materials. Portland cement, invented in the 19th century, revolutionized construction materials. Portland cement is also referred to as hydraulic cement and it comprises calcium silicates derived from for example limestone and clay, which react with water to form a solid matrix. Portland cement remains the most widely used binder in the construction industry, forming the basis of concrete, mortar, and grout.

Over time, specialty inorganic binders have been developed to meet specific requirements. For example, aluminous cements, which contain a high proportion of alumina, offer rapid strength development and resistance to high temperatures, making them suitable for applications like refractory linings.

Geopolymers represent a newer class of inorganic binders that utilize aluminosilicate materials, such as fly ash or slag, activated with alkaline solutions. Geopolymers offer advantages such as high early strength, chemical resistance, and low environmental impact compared to traditional cement-based binders. They are being explored for various applications, including construction materials and immobilization of hazardous wastes.

In recent years, contemporary research and development efforts focus on improving the performance and sustainability of inorganic binders. This includes optimizing formulations to reduce carbon emissions associated with cement production, enhancing durability to withstand harsh environments, and incorporating recycled materials to reduce waste and resource consumption.

In the development as well as in the production of inorganic binders it is well known to apply different examination method for testing of raw material composition as well as tests of various step of the production. Examples of such test methods comprises Chemical analysis techniques, such as X-ray fluorescence (XRF) spectroscopy or wet chemical analysis, mineralogical analysis techniques, such as X-ray diffraction (XRD) or optical microscopy of the cured inorganic binder.

U.S. Pat. No. 7,229,491 describes a developed geopolymer which is defined by the relative amounts of components it is formed from.

In order to assess quality parameters of the geopolymer, such as compressive strength it is required to produce and curing the geopolymer for long time, such as 28 days, which is usually applied for standard curing time in the art.

US2024083068 describes a mobile, volumetric, concrete-production system for continuous production of a fresh concrete or a batched concrete comprising a concrete mixer tank where chemicals and aggregates for the concrete are mixed. The mixed concrete is monitored by different sensors, including a camera, an acoustic sensor, a hydraulic pressure gauge, and a temperature sensor. A timeline operation sub-system is processing the data continuously to determine the quality of the concrete. The tank may be installed on a truck.

There is a need in the art for an improved or alternative method of determining or estimating binder quality associated property.

DISCLOSURE OF INVENTION

It is an objective of the present invention to provide a fast and effective method of for determining at least one property associated to a binder quality based on examination of a particulate substance comprising inorganic binder precursor particles for an inorganic binder.

In an embodiment, it is an objective to provide a reliable method of for determining at least one property associated to a binder quality based on examination of a particulate substance comprising inorganic binder precursor particles for an inorganic binder, wherein the amount of particulate substance is very small, such as even 100 grams or less.

In an embodiment, it is an objective to provide an economically and reliable method of for determining at least one property associated to a binder quality based on examination of a sample of a particulate substance comprising inorganic binder precursor particles for an inorganic binder.

In an embodiment, it is an objective to provide a method of for determining at least one property associated to a binder quality based on examination of a sample of a particulate substance comprising inorganic binder precursor particles for an inorganic binder, which method is fostering development and optimization of the inorganic binders and the production thereof.

In an embodiment, it is an objective to provide a method of for determining at least one property associated to a binder quality based on examination of a sample of a particulate substance comprising inorganic binder precursor particles for an inorganic binder, wherein the method enabling estimation of a quality property of the binder which may be obtained based on the particulate substance.

These and other objects have been solved by the invention or embodiments thereof as defined in the claims and/or as described herein below.

It has been found that the invention or embodiments thereof have a number of additional advantages, which will be clear to the skilled person from the following description.

The inventors of the present invention have found that a surprisingly effective method of determining at least one property associated to binder quality associated property based on examining inorganic binder precursor particles for an inorganic binder. Is has been found that the method is very fast, effective and reliable for determining binder quality associated property which correlated directly to inorganic binder quality parameters of an inorganic binder obtained or obtainable from the inorganic binder precursor particles, such as compressive strength, formation of pores and many further properties as described further below.

The phrase "property associated to a binder quality" is herein used to denote at least one property of the inorganic binder precursor particles, at least one property of the inorganic binder precursor particles in combination with the activator fluid or an estimated property of an inorganic binder obtained from or obtainable from the inorganic binder precursor particles or the inorganic binder precursor particles together with the activator fluid, wherein the estimated property is derived from the before mentioned properties.

The terms "user" and "operator" are used interchangeable.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other features.

Throughout the description or claims, the singular encompasses the plural and the plural encompasses the singular unless otherwise specified or required by the context.

The "an embodiment" should be interpreted to include examples of the invention comprising the feature(s) of the mentioned embodiment.

The term "substantially" should herein be taken to mean that ordinary product variances and tolerances are comprised. All features of the invention and embodiments of the invention as described herein, including ranges and preferred ranges, may be combined in various ways within the scope of the invention, unless there are specific reasons not to combine such features.

Unless other is specified, any properties, ranges of properties and/or determination and/or assay condition is given or provided at 1 atmosphere and 25° C., herein referred to as "standard condition".

The fluid substance is determined at standard condition.

All features of the invention and embodiments of the invention as described herein including ranges and preferred ranges may be combined in various ways within the scope of the invention, unless there are specific reasons not to combine such features.

The method of examining a particulate substance comprising inorganic binder precursor particles comprises determining at least one property associated to a binder quality of the particulate substance.

The method of examining the particulate substance comprising inorganic binder precursor particles comprises providing a sample mixture comprising a portion of the particulate substance and a portion of a fluid substance, performing at least one of scanning procedure, wherein each scanning procedure comprises acquiring at least one image of an image acquisition area, processing the acquired image(s) to obtain at least one processed image of each scanning procedure, and determining at least one binder quality associated property of at least the portion of the particulate substance of the particulate substance.

The phrase "property associated to a binder quality of at least the portion of the portion of particulate substance" is in the following referred to as the phrase "binder quality associated property" and these phrases are used interchangeable.

The inorganic binder precursor particles may in an embodiment comprise fresh inorganic binder precursor particles for production of a fresh binder.

The phrase "fresh inorganic binder precursor particles" means inorganic binder precursor particles that have not been subjected to a curing process and preferably is suitable for production of a fresh binder.

The phrase "fresh binder", means herein an uncured or partially uncured shapeable binder mass.

The phrase "a fully cured binder" is herein used to mean a binder cured to a stage where a further curing time of 24 hours does not result in any detectable change of compressive strength.

The phrase "a fully cured concrete" is herein used to mean a concrete comprising fully cured inorganic binder cured to a stage where a further curing time of 24 hours does not result in any detectable change of compressive strength of the concrete.

The inorganic binder precursor particles may in an embodiment comprise particles of a crushed concrete structure comprising cured inorganic binder material, which may comprise residual inorganic binder precursor particles. Preferably the determining of at least one binder quality associated property of the particulate substance of the inorganic binder precursor particles comprises determining if the portion of the residual inorganic binder precursor particles comprises uncured precursor particles and optionally comprising a quantitative and/or a qualitative determination of uncured inorganic binder precursor particle.

The qualitative determination of uncured inorganic binder precursor particles of the residual inorganic binder precursor particles may comprise determining if at least one the uncured inorganic binder precursor particles is partially or fully uncured and optionally determining the spatially location of cured portions of at least one partially uncured inorganic binder precursor particles. As it will be explained below, the determining the spatially location of cured portions of at least one partially uncured inorganic binder precursor particle may reveal if the structure from where the particles of the crushed structure is obtained has been subjected to a damage.

Advantageously, the at least one image comprises at least one light transmission image and/or at least one light reflection image.

Preferably the at least one image comprises one or more light transmission images. It has been found that the light transmission images may ensure a desired detailed 3D imaging of the inorganic binder precursor particles, which may reveal many structural details which may improve the determining of the at least one binder quality associated property of the particulate substance of the inorganic binder precursor particles.

Preferably, the particulate substance comprises at least 10% by weight of inorganic matter based on dry particulate substance, such as at least 25% by weight of inorganic matter, such as at least 25% by weight of inorganic matter, such as at least 50% by weight of inorganic matter, such as at least 75% by weight of inorganic matter, such as at least 95% by weight of inorganic matter such as 99% or more by weight of inorganic matter.

In an embodiment the method comprises mixing the portion of the particulate substance with a surplus of the fluid substance.

Heretofore, no one has considered examining inorganic binder precursor particles for determining of one or more binder quality associated property by mixing the inorganic binder precursor particles with a surplus of fluid substance, rather the particles have been examined in dry condition or the particle have been mixed with an amount of liquid substance to provide a binder and the mixture has been examined during the setting time and optionally during the hardening. The present invention thereby provides a completely new approach which has shown to be very effective and fast to determination of property associated to a binder quality of the particulate substance and where only small amounts of the particulate substance are required for the determination, such as 100 g or even less, such as 50 g or less are required.

In an embodiment the portion of the particulate substance has a weight less than the weight of the portion of the fluid substance, preferably the weight of the portion of the particulate substance is 80% or less, such than 60% or less, such than 40% or less than, such as 20% or less than, such as 15% or less than the weight of the portion of the fluid substance.

In an embodiment, the step of providing the sample mixture comprises providing the sample mixture to comprise at least 50% by weight of the fluid substance. Preferably the step of providing the sample mixture comprises providing the sample mixture to comprise at least 60%, such as at least 70%, such as at least 80%, such as at least 90%, such as at least 92% by weight of the fluid substance.

In an embodiment, the step of providing the sample mixture comprises obtaining the portion of the inorganic binder precursor particles and mixing the obtained portion of inorganic binder precursor particles with the portion of the fluid substance to provide the sample mixture to comprise at least 50% by weight of the fluid substance. Preferably the step of providing the sample mixture comprises providing the sample mixture to comprise at least 60%, such as at least 70%, such as at least 80%, such as at least 90%, such as at least 92% by weight of the fluid substance.

In an embodiment, the step of providing the sample mixture comprises obtaining the portion of the inorganic binder precursor particles and mixing the obtained portion of inorganic binder precursor particles with the portion of the fluid substance, wherein the portion of the liquid substance relative to the portion of the inorganic binder precursor particles is sufficiently large to prevent a cohesive dry unit to form within 48 hours.

Generally the binder is referred to as an inorganic binder because the reactive particles are inorganic.

The particulate substance may comprises at least 10% organic matter, for example organic polymers, such as biopolymers e.g. protein, polysaccharides and/or pectin; synthetic polymers; natural and/or synthetic rubbers, such as silicone polymers.

The organic matter may be unintentionally introduced during the manufacturing process or intentionally added for specific purposes. The method of the invention may advantageously comprise determining if the particulate substance comprises organic matter and optionally the amount and/or type of organic matter present.

Advantageously, addition of organic matter is carefully evaluated based on the desired properties of the final product, since some types of organic matter may pose challenges such as reduced strength, increased susceptibility to degradation, or altered setting times.

Examples of suitable types or organic matter are listed below:

Wood fibers: Wood fibers may intentionally be added to the particulate substance to improve the tensile strength and durability of the fully cured binder.

Cellulose-based additives: Cellulose-based materials, such as paper waste or cellulose ethers, may be intentionally added to the particulate substance enhance workability, reduce water demand, or improve adhesion.

Plant-based fibers: Fibers derived from plants like jute, sisal, or hemp may be added to the particulate substance to improve flexural strength, impact resistance, and reduce cracking of the fully cured binder.

Biochar: This is a form of charcoal produced from organic materials, such as agricultural waste or wood chips. Biochar may be used as a partial replacement for cementitious materials or as a filler to enhance certain properties like compressive strength and durability of the fully cured binder.

Rice husk ash (RHA): RHA is a byproduct of burning rice husks. It contains organic carbon and silica, which can react with calcium hydroxide to form additional cementitious compounds. It may be used as a supplementary cementitious material in the particulate substance.

Polymer additives: Organic polymers, such as lignosulfonates, polyvinyl alcohol (PVA), or polycarboxylate ethers (PCE), may be added to the particulate substance to improve workability, reduce water demand, or enhance the performance of the material.

Animal-based additives: Substances like blood meal or bone meal may be used as organic additives in the particulate substance, typically for specific applications like soil stabilization or agricultural purposes.

In an embodiment, the inorganic binder precursor particles comprises or consists of inorganic binder precursor particles in the form of geopolymeric particles comprising precursor particle for a geopolymer binder; inorganic binder precursor particles in the form of raw material particles for a hydraulic cement binder comprising un-calcined hydraulic cement precursor particles; inorganic binder precursor particles in the form of fully or partially calcined materials for a hydraulic cement binder preferably comprising clinker or crushed clinker and optionally additionally particles such as particles of Supplementary Cementitious Materials (SCM) particles and/or other additives or modifiers, such as gypsum; inorganic binder precursor particles in the form of raw material particles for a non-hydraulic cement binder, such as calcium hydroxide, magnesium hydroxide, calcium carbonate and/or other lime based material and/or clay minerals; or any mixtures comprising one or more of the above mentioned.

Examples of SCM comprises the following.

Fly Ash: Fly ash is a byproduct of coal combustion in power plants. It consists of fine particles that can be collected from the flue gases. Fly ash is rich in silica ($SiO_2$) and alumina ($Al_2O_3$) and can improve concrete workability, reduce heat of hydration, and enhance long-term strength and durability.

Silica Fume: Silica fume, also known as microsilica, is a byproduct of silicon and ferrosilicon alloy production. It is an ultrafine powder that consists of amorphous silicon dioxide ($SiO_2$). Silica fume has high pozzolanic activity and can improve concrete strength, impermeability, and resistance to chemical attack.

Ground Granulated Blast Furnace Slag (GGBFS): GGBFS is a byproduct of iron production in blast furnaces. It consists primarily of silicates and aluminosilicates and exhibits cementitious properties when finely ground. GGBFS can enhance concrete workability, reduce heat of hydration, and improve sulfate resistance and durability.

Natural Pozzolans: Natural pozzolans, such as volcanic ash or calcined clay, are naturally occurring materials that contain reactive silica and alumina. They can improve concrete strength, reduce permeability, and enhance sulfate resistance.

Limestone Powder: Limestone powder is a finely ground material derived from limestone quarries. It is sometimes used as an SCM to improve concrete workability and reduce the heat of hydration.

Gypsum may primarily serve as a setting regulator and does not significantly affect the long-term performance or properties of concrete.

The particulate substance may comprises support particles, such as one or more of fillers, modifiers, plasticizers and/or activator particles.

The phrase "activator particles" means herein particles in undissolved condition, which upon dissolution form an activator liquid solution".

The phrase "Support particles" means herein particles that may support, activate or in other way influence the inorganic binder precursor particles.

In an embodiment, the fluid substance comprises a substance expected to induce a physical or chemical reaction involving at least some of the inorganic binder precursor particles of the sample mixture.

Advantageously, the fluid substance comprises an activator fluid. The fluid substance comprising the activator may in an embodiment be an activator fluid that is mixed with the portion of the particulate substance to obtain the sample mixture. In an embodiment, the fluid substance comprising the activator may be obtained by adding a fluid, such as an aqueous fluid to the portion of the particulate substance to obtain the sample mixture, wherein the portion of the particulate substance comprises activator particles which is dissolved by the added fluid.

The phrase "activator fluid" means herein a fluid that is capable of activating or providing the inorganic binder precursor particles to initiate reaction towards formation of an at least partially cured binder.

A suitable activator fluid depend largely on the inorganic binder precursor particles.

Examples of suitably activator fluids are listed in table 1.

TABLE I

| Inorganic binder precursor particles | Example of activator fluid |
| --- | --- |
| Geopolymeric particles | Any acidic or preferably alkaline fluid, preferably in liquid form. |
| Raw material particles for a hydraulic cement binder | Only static properties are determined on this raw material |
| Particles comprising fully or partially calcined materials for a hydraulic cement binder | Any aqueous liquid, such as water. Any other fluid inducing hydration of the calcined material. |
| Raw material particles for a non-hydraulic cement binder | Carbon-dioxide, e.g. in the form of gas or gas bubbles through a liquid. An aqueous liquid containing carbonic acid. Any other fluid inducing carbonation. |
| Mixtures of the above mentioned inorganic binder precursor particles | One or more of the activator fluid for the respective type of inorganic binder precursor particles. |

Further examples will be clear from the description below.

Where the at least one binder quality associated property comprises a dynamic binder quality associated property, it is preferred that the fluid substance comprises a substance expected to induce a physical or chemical reaction involving at least some of the inorganic binder precursor particles of the sample mixture.

In an embodiment, the fluid substance comprises a dispersion fluid for dispersing the particulate substance. The dispersion fluid is suitable for spreading out the portion of the particulate substance, which may ensure a desired view of the individual particles.

The fluid substance may for example comprise an aqueous liquid and/or oil, for example organic solvents or water optionally comprising surfactants.

Surfactants, such as Tween, Triton, or cetyltrimethylammonium bromide (CTAB), may be used to stabilize particle dispersions.

In an embodiment, the fluid substance comprises a polymer solutions, such as polyvinyl alcohol (PVA) or polyethylene glycol (PEG), may be used for dispersion.

Further information about dispersion of the portion of particulate substance may be found in co-pending patent application DK PA 202370385.

The at least one at least one property associated to a binder quality of at least the portion of particulate substance is in the following referred to as"the binder quality associated property".

The at least one binder quality associated property may comprises a static property and/or a change property. The phrase "static property" means herein a property that remain static during the examination, e.g. because the inorganic binder precursor particles are not subjected to an activator fluid. The phrase "change property" means herein a property that changes during the examination, e.g. because the inorganic binder precursor particles are subjected to an activator fluid.

In an embodiment, the at least one binder quality associated property of at least the portion of the particulate substance comprises a geometric property, such as morphology, particle size, particle size distribution, particle volume, particle volume distribution, particle shape, specific surface area, external surface area.

The geometric property may be static or dynamic as explained further below.

In an embodiment, the at least one binder quality associated property of at least the portion of the particulate substance content property, such as an optical property, classification of particles, a purity characteristic, a quantification of one or more particle types, a property associated to an amount or a relative amount of one or more components and/or aggregates of the particulate substance, such as content of calcined and/or carbonated components and/or content of mineral types and/or one or more of alumina moieties and silicate moieties.

In an embodiment, the geometric property comprises a deterioration property, such as a property associated to cracking, crazing, blistering, delamination, curling, efflorescence, chipping, spalling, formation of holes, freeze-thaw effects, scaling, and/or roughness of the particles.

In an embodiment, the geometric property comprises a geometric static property, such as such as morphology, particle size, particle size distribution, particle volume, particle volume distribution, particle shape, specific surface area, external surface area of the portion of the substance and/or a deterioration property, such as roughness, cracks and/or holes.

In an embodiment, the geometric property comprises a geometric change property, such as a change of morphology, such as a change of particle size, a change of particle size particle size distribution, a change of particle size particle volume, a change of particle size particle volume distribution, a change of particle size particle shape, a change of particle size specific surface area, a change of particle size external surface area and/or a deterioration property, such as a change of roughness, a change revealing cracks and/or a change revealing other defects.

The geometric static property may advantageously be a geometric static property of fresh inorganic binder precursor particles e.g. to determine a uniformity and/or quality of the precursor particles.

In an embodiment, the geometric static property is a geometric static property for particles of a crushed cured structure expected to comprise and preferably comprising residual inorganic binder precursor particles, wherein the geometric static property for example comprises determining if the particles comprises high or uneven roughness which may provide an indication of a deterioration property, porosity and/or homogeneity of the structure.

The content property may in an embodiment comprise a content static property, such as an optical property, e.g. transparence and/or color, such as classification of particles, a purity characteristic, a quantification of one or more particle types, a property associated to amount or relative amount of one or more mineral types and/or one or more of alumina moieties and silicate moieties.

The content property may in an embodiment comprise a content change property, such as a change of an optical property, e.g. a change of transparence and/or a change of color, such as a change of amount or a change of relative amount of one or more mineral types and/or one or more of alumina moieties and silicate moieties.

It has been found that the method of the invention may be applied to ensure a very reliable estimation of one or more qualities of a binder obtainable from the inorganic binder precursor particles. The estimation of one or more qualities of a binder obtainable from the inorganic binder precursor particles may be based on one or more binder quality associated properties such as comprising a content property e.g. material composition. In an embodiment, In an embodiment, the at least one binder quality associated property comprises a property related to an estimated quality of a binder obtainable from the inorganic binder precursor particle. The estimation of one or more qualities of a binder obtainable from the inorganic binder precursor particles may be based on one or more binder quality associated properties comprising one or more of reactivity of inorganic binder precursor particles e.g. comprising, material composition of the inorganic binder precursor particles, morphological properties of the inorganic binder precursor particles, activation properties, carbonation and/or calcination properties.

In an embodiment, the at least one binder quality associated property comprises one or more estimated qualities of a binder obtainable from the inorganic binder precursor particles, such as setting time, curing level as a function of time, porosity, estimated bearing capacity and/or compressive strength over time after activation, such as after 10 minutes, such as after 1 hour, such as after 2 hours, such as after 4 hours, such as after 5 hours and/or after 28 days as well as any other static and/or change properties of the particles.

The term "curing level" is herein used to mean level of reaction from activation to a selected stage of curing, e.g. to a selected strength of the binder has been reached and/or until a reached strength is not increasing further over a selected time slot.

The one or more estimated qualities may comprise estimation of compressive strength, tensile strength, flexural strength, shear strength, bond strength, durability-related strengths.

The method may conveniently comprise modifying the material composition and/or morphological properties, such as particle sizes of the inorganic binder precursor particles and/or modifying the process of obtaining the binder, such as modifying the activation, carbonation and/or calcination process based on the at least one binder quality associated property to thereby increasing the obtainable binder quality associated property.

For example where binder one or more quality associated property results in an estimation of quality of a binder obtainable from the inorganic binder precursor particle which is below a selected threshold, e.g. where the setting time is to slow, the obtainable compressive strength is too low etc., the material composition of the inorganic binder precursor particles, the particle sizes of the inorganic binder precursor particles may be reduced by grinding, the inorganic binder precursor particles may be subjected to a heat treatment e.g. to increase the calcination level and/or a different activat0r fluid may be applied. Thereby the method may be applied to provide a desired recipe for providing a binder with desired qualities, including determining a composition of particulate substance to provide the binder, a process for optional pretreatment of the particulate substance or a part thereof to provide the binder and/or a process for the production of the binder.

In an embodiment, the binder quality associated property comprises a static property, such as a geometric static property and/or a content static property, and wherein the method comprises selecting the portion of the fluid substance to be non-reactive and/or non-dissolving of at least the inorganic binder precursor particles and optional activator particles of the particulate substance In an embodiment, the at least one property associated to the binder quality associated property comprises a change property, such as a geometric change property and/or a content change property, and wherein the method preferably comprises selecting the portion of the fluid substance to comprise an activator fluid.

In an embodiment, the at least one property associated to the binder quality associated property comprises a combined content and geometric property, such as a combined content and geometric static property and/or a combined content and geometric change property.

Advantageously, the performing of at least one of scanning procedure comprises performing a plurality of scanning procedures, wherein each scanning procedure comprises acquiring a least one light transmission image and/or a light reflection image of an image acquisition area, wherein the plurality of scanning procedures comprises at least two scanning procedures, such as at least 5 scanning procedures or more.

The method may for example comprise one or more scanning procedures for a static property followed by a plurality of scanning procedures for a change property, such as reactivity In an embodiment, the inorganic binder precursor particles comprises or consists of inorganic binder precursor particles in the form of geopolymeric particles. The binder quality associated property may advantageously comprise a geopolymerization associated property, preferably a geopolymerization reactivity.

In this embodiment it is desired that the geopolymeric particles comprises precursor particle for a geopolymer binder and wherein the particulate substance comprises at least one of calcined clay, e.g. such that it is known in the art.

In an embodiment, geopolymeric particles comprises ore or more of calcined clay silicates, red clay, kaolin, metakaolin, bentonite, halloysite, illite, ball clay, attapulgite and paygorskite; ash, such as fly ash, rice husk ash, coal fly ash, incinerator ash, volcanic ash, sewage sludge ash, cassava peel ash, rise husk ash, calcium fly ash, ground granulated blast furnace slag, olive biomass fly ash, palm oil fuel ash and municipal solid waste incineration fly ash; slag, such as granulated blast furnace slag (GBFS), metal slag e.g. nickel slag and/or steel slag; grog, such as coal grog or ceramic grog; mullite; diatomit; silica fume; glass powder (e.g. quartz powder); glass wool residue; iron ore tailing; zeolite; bauxite residues (red mud); bauxite ore tailing; and/or magnesium; brick waste.

Generally it is desired that the geopolymeric particles comprises a source of alumina and a source of silicate. Preferable the geopolymeric particles comprises aluminosilicate.

Where the inorganic binder precursor particles comprises geopolymeric particles and the fluid substance is a dispersion liquid, the dispersion liquid may conveniently be an aqueous liquid and/or an oil, for example an organic solvent optionally comprising surfactants.

Where the inorganic binder precursor particles comprises geopolymeric the fluid substance is advantageously an activator liquid capable of activation polymerization of the geopolymeric particles The at least one geopolymerization associated property may be a static property or a change property, wherein a static property means herein a property that remain static during the examination, e.g. because the geopolymeric particles are not subjected to an activator liquid and wherein a change property means herein a property that changes during the examination, e.g. because the geopolymeric particles are subjected to an activator liquid.

In an embodiment, where the inorganic binder precursor particles comprises geopolymeric particles and the particulate substance comprises support particles, the support particles are at least partly dissolvable in the portion of liquid substance and wherein the determining of the at least one property associated to a binder quality of the particulate substance comprises determining one or more parameters associated to the solvability of the support particle, preferably the support particle comprises activator particles.

The activator particles may for example comprise one or more of

Sodium Hydroxide (NaOH), in the form of granules or pellets;

Potassium Hydroxide (KOH), in the form of granules or pellets;

Sodium Silicate (Sodium Water Glass), in the form of powder;

Potassium Silicate (Potassium Water Glass), in the form of powder;

Sodium Carbonate (Soda Ash), in the form of granules or pellets;

Potassium Carbonate ($K_2CO_3$), in the form of granules or powder.

Where the support particles comprises alkali metal oxide Silicate (Water Glass), such as Potassium Silicate and/or sodium Silicate, the support particles may serve as an additional source of silicates for the geopolymerization.

In an embodiment, where the inorganic binder precursor particles comprises geopolymeric particles, the portion of fluid substance is preferably a liquid substance advantageously comprising a substance expected to provide an activator liquid, such as an alkaline activator liquid or an acidic activator liquid, preferably the portion of liquid substance comprises the activator liquid and/or wherein the activator liquid is formed upon dissolving of activator particles.

The alkaline activator liquid provides hydroxide ions (OH—) that react with the source materials to release aluminum and silicon species. These species then undergo condensation reactions, forming polymeric chains and three-dimensional networks. The reaction is exothermic, meaning it releases heat during the process.

In an embodiment the activator liquid is an acidic activation solution, such as an acidic activation solution comprising phosphoric acid, phosphate, citric acid, acetic acid, and/or formic acid.

When an acidic activator is used, the source materials containing aluminosilicates react with the acidic solution instead of an alkaline one. The acid can provide protons (H+) that react with the aluminosilicates, leading to the dissolution of these materials and the subsequent formation of the geopolymeric structure.

The activator liquid may preferably comprises a solution of one or more of Sodium Hydroxide (NaOH), Potassium Hydroxide (KOH), alkali metal oxide Silicate (Water Glass), Sodium Carbonate (Soda Ash), Potassium Carbonate ($K_2CO_3$).

Where the activation solution comprises a solution of alkali metal oxide Silicate (Water Glass), such as Potassium Silicate and/or sodium silicate, the alkali metal oxide Silicate may serve as an additional source of silicates for the geopolymerization. The alkali metal oxide silicate thereby has a dual role as an alkali source and as a silica source, allowing for lower molar concentrations than where for example sodium hydroxide is used.

In an embodiment, the activator liquid comprises a mixture of alkali metal hydroxide and alkali metal oxide silicate.

Once the binder precursor particles comprising geopolymeric particles is mixed with the activator liquid, e.g. an alkaline activator solution, the activator liquid start to react with reacts with the silicon (Si) and aluminum (AI) species present in the binder precursor particles. This reaction leads to the dissolution of these species, forming reactive species such as silicate and aluminate ions. The dissolution may be detected by the method of the invention. This dissolution step of the geopolymerisation is decisive for the final geopolymeric binder and based on determination performed during this dissolution step, highly reliable estimation of one or more qualities of the geopolymeric binder may be estimated e.g. as described above.

The dissolved silicate and aluminate ions undergo poly-condensation reactions, where they polymerize and cross-link to form a three-dimensional network structure. This network structure is the geopolymer binder, which provides the binding strength and durability to the material. As the polymerization reactions progress, the geopolymer mixture undergoes a setting process, during which it transitions from a liquid or semi-liquid state to a solidified form. The setting time and hardening of the geopolymer depend on factors such as the composition of the precursor materials, the concentration of the activator solution, and environmental conditions (e.g., temperature).

After setting, the geopolymer material may be further under controlled conditions (e.g., elevated temperature and humidity) to enhance its strength and durability over time. Curing helps promote further chemical reactions and the development of the geopolymer structure.

In an embodiment, the inorganic binder precursor particles comprises or consists of inorganic binder precursor particles in the form of raw material particles for a hydraulic cement binder comprising un-calcined hydraulic cement precursor particles, and wherein the binder quality associated property comprises a cement quality associated property, preferably a cement associated reactivity.

The raw material particles for a hydraulic cement binder may for example comprise sand; shale; clay, such as clay silicates, red clay, kaolin, metakaolin, bentonite, halloysite, illite, ball clay, attapulgite and paygorskite; ash, such as fly ash, rice husk ash, coal fly ash, incinerator ash, volcanic ash, sewage sludge ash, cassava peel ash, rise husk ash, calcium fly ash, ground granulated blast furnace slag, olive biomass fly ash, palm oil fuel ash and municipal solid waste incineration fly ash; slag, such as granulated blast furnace slag (GBFS), metal slag e.g. nickel slag and/or steel slag; metal ore, such as iron ore; grog, such as coal grog or ceramic grog; mullite; diatomit; silica fume; glass powder (e.g. quartz powder); glass wool residue; iron ore tailing; zeolite; bauxite residues (red mud); bauxite ore tailing; brick waste; gypsum and/or magnesium.

In an embodiment, where the inorganic binder precursor particles raw material particles for a hydraulic cement binder, the fluid substance is a liquid substance, preferably a dispersion liquid, such as an aqueous liquid and/or an oil, for example an organic solvent optionally comprising surfactants.

The at least one cement associated property for the raw material particles for a hydraulic binder may advantageously be a static property In an embodiment, the inorganic binder precursor particles comprises or consists of inorganic binder precursor particles in the form of fully or partially calcined material particles for a hydraulic cement binder preferably comprising clinker or crushed clinker and optionally additionally particles such as particles of Supplementary Cementitious Materials (SCM) particles and/or other additives or modifiers, such as gypsum.

The fully or partially calcined material particles for a hydraulic cement binder comprises raw material particles for the hydraulic cement binder which advantageously have been subjected to a calcination process, wherein the raw material particles, preferably comprises sand; shale; clay, such as clay silicates, red clay, kaolin, metakaolin, bentonite, halloysite, illite, ball clay, attapulgite and paygorskite; ash, such as fly ash, rice husk ash, coal fly ash, incinerator ash, volcanic ash, sewage sludge ash, cassava peel ash, rise husk ash, calcium fly ash, ground granulated blast furnace slag, olive biomass fly ash, palm oil fuel ash and municipal solid waste incineration fly ash; slag, such as granulated blast furnace slag (GBFS), metal slag e.g. nickel slag and/or steel slag; metal ore, such as iron ore; grog, such as coal grog or ceramic grog; mullite; diatomit; silica fume; glass powder (e.g. quartz powder); glass wool residue; iron ore tailing; zeolite; bauxite residues (red mud); bauxite ore tailing; brick waste; gypsum and/or magnesium.

Advantageously, the fully or partially calcined material particles for a hydraulic cement binder comprises Supplementary Cementitious Materials (SCM) particles and/or other additives or modifiers, such as gypsum which may be added prior to or after the calcination process.

Where the inorganic binder precursor particles comprises fully or partially calcined material particles for a hydraulic cement binder, the binder quality associated property advantageously comprises a cement quality associated property, preferably a cement associated reactivity, such as calcination quality, calcination level optionally of individual particle or types of particles. The calcination quality and/or calcination level may for example be determined by generating a hyperspectral image from one or more scanning procedures as described below.

Where the inorganic binder precursor particles comprises fully or partially calcined material particles for a hydraulic cement binder, the fluid substance may conveniently be a dispersion liquid, such as a water free substance, such as oil or an organic fluid.

In an embodiment where the inorganic binder precursor particles comprises fully or partially calcined material particles for a hydraulic cement binder, the fluid substance is advantageously an activator liquid capable of initiating dissolving and optionally hydration reaction of the particulate substance towards formation of the hydraulic cement, the activator liquid preferably comprises water.

This dissolution and hydration step of the hydraulic cement process is decisive for the final hydraulic cement binder and based on determination performed during this dissolution step anda7or the hydration step, highly reliable estimation of one or more qualities of the hydraulic cement binder may be estimated e.g. as described above.

The at least one cement quality associated property may be a static property or a change property, wherein a static property means herein a property that remain static during the examination, e.g. because the fully or partially calcined material particles for a hydraulic cement binder are not subjected to an activator fluid and wherein a change property means herein a property that changes during the examination, e.g. because the fully or partially calcined material particles for a hydraulic cement binder are subjected to an activator fluid.

The production of hydraulic cement is well known in the art and has developed over hundreds of years. The chemistry involved is very complex and minor modifications, such as a modification of the raw material precursor particles, particle sizes, calcination process, such as temperature or time etc., addition of additives and/or modifiers before or after calcination may have large influence of the final quality of the hydraulic cement.

A typical method of producing hydraulic cement comprises mixing and grinding the raw materials to obtain the inorganic binder precursor particles in the form of raw material particles for a hydraulic cement binder.

The of raw material particles for a hydraulic cement binder may then be mixed with suitably additives and/or or modifiers such as the additive/modifiers described above.

Thereafter the raw material particles optionally mixed with additives and/or or modifiers are subjected to a calcination process usually by heat treatment in a kiln.

The calcination process is extremely energy consuming and methods that may lead to optimization of the process while potentially reducing the required energy consumption will be of extremely high value both is respect of saved cost but also in respect of reducing carbon dioxide emission.

The calcination process may be the most important step of the production of hydraulic cement.

The calcined particles resulting directly from the calcination process are normally called clinker and comprises typically small, irregularly shaped nodules in a few millimeters to centimeters in size.

Once the clinker is cooled, it is ground into a fine powder and optionally mixed with additives and/or or modifiers e.g. as described above.

In an embodiment, the inorganic binder precursor particles comprises or consists of inorganic binder precursor particles in the form of raw material particles for a nonhydraulic cement binder, such as limestone or other sources of non-hydraulic lime, clay, calcium hydroxide, magnesium hydroxide, calcium carbonate and/or other lime based material and/or clay minerals.

Where the inorganic binder precursor particles comprises raw material particles for a non-hydraulic cement binder, the binder quality associated property comprises a non-hydraulic cement quality associated property, preferably a non-hydraulic cement associated reactivity, such as carbonation quality and/or carbonation level optionally of individual particle or types of particles.

Where the inorganic binder precursor particles comprises raw material particles for a non-hydraulic cement binder, the fluid substance may be a dispersion liquid, such as an aqueous liquid and/or an oil, for example an organic solvent optionally comprising surfactants.

In an embodiment, where the inorganic binder precursor particles comprises raw material particles for a non-hydraulic cement binder, the fluid substance may be an activator fluid such as a carbon dioxide and/or carbonic acid containing fluid capable of initiating reaction towards formation of a binder comprising non-hydraulic cement.

The at least one binder quality associated property may be a static property or a change property, wherein a static property means herein a property that remain static during the examination, e.g. because the raw material particles for a non-hydraulic cement binder are not subjected to an activator fluid and wherein a change property means herein a property that changes during the examination, e.g. because the raw material particles for a non-hydraulic cement binder are subjected to an activator fluid.

Generally the carbonation process is a relative slow process. However, the carbonation process may be accelerated by increasing the amount of available carbon dioxide and/or by increasing the temperature.

In an embodiment, the inorganic binder precursor particles comprises a particle mixture comprising a first portion of inorganic binder precursor particles in the form of fully or partially calcined material particles for a hydraulic cement binder and a second portion comprising geopolymeric particles and/or raw material particles for a non-hydraulic cement binder, and wherein binder quality associated property comprises a property associated to the reactivity and/or a strength parameter of the particle mixture and wherein the method comprises providing samples from two or more particulate substances with different relative amounts of the first and the second portion and examining each of the samples and based thereon determining a particle mixture with a desired reactivity and/or a strength parameter.

The strength parameter may preferably comprise at least one of density, porosity compressive strength, tensile strength, flexural strength, shear strength, bond strength and/or durability-related strengths.

By providing the binder to be hybrid binder in the form of a combination of a hydraulic cement binder and one or both of a geopolymeric binder (due to the content of the geopolymeric particles) and a non-hydraulic cement binder (due to the content of the raw material particles for a non-hydraulic cement binder) a hybrid binder with a desired combination of properties may be obtained. By use of the method of the invention, development of such hybrid binders may be developed and optimized much faster since the qualities of the hybrid binder may be estimate based on determinations of property associated to a binder quality of portions of the respective portions of particles.

Advantageously, the performing of the at least one of scanning procedure comprises performing a set of scanning procedures comprising at least two scanning procedures, each scanning procedure of the set of scanning procedures comprises illuminating at least the image acquisition area of the sample mixture by a light source, wherein the light source differs in wavelength from a first of the two scanning procedures to another of the at least two scanning procedures.

In an embodiment, the set of scanning procedure comprises from 3 to 10, such as from 4 to 8 scanning procedures, wherein the wavelengths of the light sources applied in the respective scanning procedures differs from one scanning procedure to another, preferably the respective light sources have different center wavelength, such as center wavelengths in the range of from 380 nm to 1000 nm, such as comprising at least one 465 nm, 565 nm, 590 nm, 626 nm, 880 nm, preferably the respective light sources has a spectral bandwidth, which is about 10 nm or less, such as about 5 nm or less.

The spectral bandwidth may be defined by its full width at half maximum (FWHM).

FWHM means the width of the wavelength range at which the intensity is equal to or greater than half of the maximum intensity.

The center wavelengths are preferably in the visible range from 380 nm to 750 nm and/or in the near infrared range from 750 nm to 1000 nm. Preferably the center wavelengths of the respective light sources are selected such that the emitted light is reflected/absorbed differently by different chemical elements or materials expected to be present in the inorganic binder precursor particles. Thereby various chemical components of the inorganic binder precursor particles, such as non-calcined limestone, various minerals, such as alumina moieties, silicate moieties, silica ($SiO_2$), alumina ($Al_2O_3$), dicalcium silicate (C2S), tricalcium aluminate (3A), tetracalcium aluminoferrite (C4AF), tricalcium silicate (C3S), dicalcium silicate (C2S), tricalcium aluminate (C3A), tetracalcium aluminoferrite (C4AF) or other reaction products of the calcination.

In an embodiment, the at least one processed image of each scanning procedure of the set of scanning procedures comprises absorbance data and wherein method further comprises combining the absorbance data for two or more of the processed image to provide a hyperspectral image.

Advantageously, the determination of the at least one binder quality associated property of the particulate substance comprises determining at least one content property, such as qualitatively or quantitatively determining one or more minerals and/or other chemical components, such as alumina moieties, silicate moieties, silica ($SiO_2$), alumina ($Al_2O_3$), dicalcium silicate (C2S), tricalcium aluminate (3A), tetracalcium aluminoferrite (C4AF), tricalcium silicate (C3S), dicalcium silicate (C2S). tricalcium aluminate (C3A), tetracalcium aluminoferrite (C4AF) or other reaction products of the calcination, wherein the method optionally comprises classifying the particles based on the absorbance data, such as based on their content of and/or determining at least one geometric property and/or a combined content and geometric static property based on the absorbance data, such as determining a spatial location and or distribution of one or more mineral types and/or one or more of alumina moieties and silicate moieties.

The determining of at least one content property, such as qualitatively or quantitatively determining one or more minerals may be very beneficial especially where the particulate substance comprises precursor particle for a geopolymer binder, raw material particles for a hydraulic cement binder comprising un-calcined hydraulic cement precursor particles and/or fully or partially calcined material particles for a hydraulic cement binder.

For example for precursor particle for a geopolymer binder, where the alumina moieties and/or the silicate moieties appears to be insufficient for an effective geopolymerization, the particulate substance may be supplemented with additional particles comprising alumina moieties and silicate moieties.

Where a major part of the alumina moieties and/or the silicate moieties may be encapsulated in the particles and thus may not be available for the geopolymerization process, it may be desired to crush the particulate substance to obtain smaller particles and thereby an increased specific surface area of the geopolymeric particles, whereby more of the alumina moieties and silicate moieties may be available for the geopolymerization.

The determining of at least one content property, such as qualitatively or quantitatively determining one or more minerals may be very beneficial where the geopolymeric particles comprises particles of a crushed geopolymer structure portion, such as a crushed sample of a geopolymer structure. This may for example be used to qualitatively or quantitatively determining remaining alumina moieties and silicate moieties, which may be applied for determining the potential of reuse of the geopolymer structure as a source of alumina moieties and silicate moieties in fresh geopolymers In an embodiment, where the particulate substance comprises geopolymeric particles comprises particles of a crushed geopolymer structure portion and the determining of at least one content property, such as qualitatively or quantitatively determining one or more minerals comprises determining a spatial location and or distribution of one or more mineral types and/or one or more of alumina moieties and silicate moieties. By analyzing the spatial location and or distribution of one or more mineral types and/or one or more of alumina moieties and silicate moieties it may be determined if the geopolymer structure has been subjected to chemical and/or mechanical attacks that may result in a reduce strength or other weaknesses of the geopolymer structure.

For example where the particulate substance comprises fully or partially calcined material particles for a hydraulic cement binder, it may be determined if the particulate substance is sufficient calcined or if the calcination is insufficient. This may for example be remedied by increasing the calcination temperature and/or the calcination time or by adding precursor particle for a geopolymer binder, by adding raw material particles for a non-hydraulic cement binder and/or by adding additives and/or or modifiers e.g. as described above e.g. Natural Pozzolans. Where it is determined that the calcination is sufficient, it may be tried to reduce the calcination temperature and/or the calcination time to reduce the carbon dioxide footprint.

The determining of at least one content property, such as qualitatively or quantitatively determining one or more minerals may be very beneficial where the inorganic binder precursor particles comprises particles of a crushed cement containing structure portion, such as a crushed sample of a concrete structure. This may for example be used to qualitatively or quantitatively determining remaining uncured calcined particles, which may be applied for determining the potential of reuse of the concrete structure as a source for particulate supplements in the production of fresh hydraulic cement or as a source for other types of inorganic binders or concretes.

In an embodiment, where the particulate substance comprises geopolymeric particles comprises particles of a crushed sample of a concrete structure and the determining of at least one content property comprises determining a spatial location and or distribution of one or more such as alumina moieties, silicate moieties, silica ($SiO_2$), alumina ($Al_2O_3$), dicalcium silicate (C2S), tricalcium aluminate (3A), tetracalcium aluminoferrite (C4AF), tricalcium silicate (C3S), dicalcium silicate (C2S), tricalcium aluminate (C3A), tetracalcium aluminoferrite (C4AF) or other reaction products of the calcination. By analyzing the spatial location and/or distribution of such components, it may be determined if the concrete structure has been subjected to chemical and/or mechanical attacks that may result in a reduce strength or other weaknesses of the concrete structure.

In an embodiment, the method comprises obtaining a plurality of hyperspectral images over a time period, wherein each hyperspectral images is associated to a time attribute, wherein the portion of liquid substance comprises an activator fluid and wherein the determination of the at least one binder quality associated property of the particulate substance comprises determining at least one content change property based on one or more differences of absorbance data between two or more of the hyperspectral images obtained over the time period and associated to different time attributes, such as a change of content of one or more minerals or one or more mineral types, such as alumina moieties, silicate moieties, silica ($SiO_2$), alumina ($Al_2O_3$), dicalcium silicate (C2S), tricalcium aluminate (3A), tetracalcium aluminoferrite (C4AF), tricalcium silicate (C3S), dicalcium silicate (C2S), tricalcium aluminate (C3A), tetracalcium aluminoferrite (C4AF) or other reaction products of the calcination.

Wherein each hyperspectral images is associated to a time attribute which for a respective hyperspectral image thereof represents a time of performing the set of scanning procedures for this respective hyperspectral image. This may for example be the time of starting, the time of ending or a median time of performing the set of scanning procedures.

In an embodiment, the method comprises obtaining a plurality of hyperspectral images over a time period, wherein each hyperspectral images is associated to a time attribute, wherein the portion of liquid substance comprises an activator fluid and wherein the determination of the at least one binder quality associated property of the particulate substance comprises determining at least one geometric property and/or a combined content and geometric change property based on one or more differences of absorbance data between two or more of the hyperspectral images obtained over the time period and associated to different time attributes, such as a change of content of one or more minerals or one or more mineral types and/or one or more of alumina moieties and silicate moieties and/or spatial location and/or distribution of the change(s).

In an embodiment, the determining of at a change of content of one or more minerals or one or more mineral types may be applied to determine a reactivity of the particulate substance.

In an embodiment, where the particulate substance comprises a particles of a crushed structure portion comprising cured binder, such as a crushed sample of a geopolymer structure or a concrete structure, the determining of spatial location and/or distribution of change(s) of content of one or more minerals or one or more mineral types and/or one or more of alumina moieties and silicate moieties, may be applied to determine if the crushing has exposed new surfaces with a content alumina moieties and silicate moieties, such as silica ($SiO_2$), alumina ($Al_2O_3$), dicalcium silicate (C2S), tricalcium aluminate (3A), tetracalcium aluminoferrite (C4AF), tricalcium silicate (C3S), dicalcium silicate (C2S). tricalcium aluminate (C3A), tetracalcium aluminoferrite (C4AF) or other reaction products of the calcination, which over the time period has been fully or partially dissolved by the activation solution or if the crushing has a lower fraction of exposed new surfaces with a content alumina moieties and silicate moieties than expected e.g. by combining with a reference. Thereby it may be determined if the structure has been subjected to chemical and/or mechanical attacks that may have resulted in that cracks, holes and/or cavitations together with an alkaline solution e.g. due to a combination of salt and water has damaged the structure and washed out valuable minerals or portions thereof from the structure.

In an embodiment, the performing of the at least one of scanning procedure comprises performing a plurality of scanning procedures, over an activation time period and for each scanning procedure obtaining at least one processed image, wherein the processed image(s) for each scanning procedures comprises a set of absorbance data and is associated to a time attribute, wherein the portion of liquid substance comprises an activator fluid and wherein the determination of the at least one binder quality associated property of the substance comprises determining at least one geometric change property, such as a change of particle size, a change of particle size particle size distribution, a change of particle size particle volume, a change of particle size particle volume distribution, a change of particle size particle shape, a change of particle size specific surface area, a change of particle size external surface area and/or a deterioration property, such as a change of roughness, a change revealing cracks and/or a change revealing other defects.

For example, the at least one binder quality associated property of the particulate substance comprises determining at least one deterioration property based on one or more differences of absorbance data between two or more of the processed images associated to different time attributes.

In an embodiment, the determination of the at least one binder quality associated property of the particulate substance comprises determining at least one geometric change property based on one or more differences of absorbance data between two or more of the processed images associated to different time attributes.

For example, the determination of the at least one binder quality associated property of the particulate substance may comprise qualitatively or quantitatively determining particle dissolution, such as determining fraction dissolved of a selected group of particles of the scanned sample mixture of the particulate substance, such as a fraction by area, a fraction by volume, a fraction by percentage, a fraction by number of particles, or any combinations comprising one or more of these.

In an embodiment, the method comprises quantitatively determining fraction dissolved of a selected group of particles of the scanned sample mixture of the particulate over at least a part of the activation time period and preparing a dissolution time profile representing the fraction dissolved as a function of time.

In an embodiment, the method further comprises estimating a quality parameter such as a strength parameter of an at least partly cured inorganic binder obtained or obtainable from the particulate substance, wherein the estimation is based on the dissolution time profile representing the fraction dissolved as a function of time, preferably the strength parameter is selected from compressive strength, tensile strength, flexural strength, shear strength, bond strength and/or durability-related strengths.

In an embodiment, the method comprises preparing a the dissolution time profile representing the fraction dissolved as a function of time to be a reference dissolution time profile representing the fraction dissolved as a function of time of a portion of reference particulate substance where one or more qualities of a final binder obtainable from the reference particulate substance are known.

Preferably, the method comprises preparing two or more reference dissolution time profiles for respective reference particulate substances.

In an embodiment, the estimating of the quality parameter, such as a strength parameter comprises correlating one or more particle dissolution determinations of one or more portions of the particulate substance to one or more of the reference dissolution time profiles.

The estimation of the strength parameter of the at least partly cured binder obtained or obtainable from the particulate substance may for example be an estimation of the strength parameter at a selected time after activation such as after 10 minutes, after 1 hour or after 28 days.

In an embodiment, the method comprises estimating a compressive strength of an at least partly cured inorganic binder obtained or obtainable from the particulate substance, wherein the estimation is based on the dissolution time profile representing the fraction dissolved as a function of time such as the reference dissolution time profile representing the fraction dissolved as a function of time.

It has been found that the dissolution time profile representing the fraction dissolved as a function of time usually comprises a plateau. Advantageously, the estimation is based on the plateau of the dissolution time profile representing the fraction dissolved as a function of time.

Generally an inorganic binder will have fully cured to reach its final compressive strength after 4 weeks at 20° C. Where the particulate substance comprises raw material particles for a non-hydraulic cement binder the curing process may be slower. At higher temperature, the curing goes faster and at lower temperature the curing may go slower.

The phrase "a fully cured inorganic binder" is herein used to mean an inorganic binder cured to a stage where a further curing time of 24 hours does not result in any detectable change of compressive strength.

In an embodiment, the method comprises estimating a curing time at a selected curing condition to reach a selected compressive strength of an inorganic binder obtained or obtainable from the particulate substance.

The curing condition preferably comprises temperature.

In an embodiment, the method further comprises estimating a compressive strength of a partially cured inorganic binder obtained or obtainable from the particulate substance, wherein the dissolution time profile representing the fraction dissolved as a function of time comprises a progression phase, wherein the estimation is based on the progression phase of the dissolution time profile representing the fraction dissolved as a function of time. Preferably the compressive strength of the partially cured inorganic binder comprises a setting compressive strength.

The progression phase may comprise a linear progression or an exponential progression.

In an embodiment, the plurality of scanning procedures, over a time period is obtained at a condition, such as a selected. Preferably the selected condition comprises at least one of a temperature and an activation fluid in the form of the portion of liquid substance of the sample mixture, wherein the condition preferably comprises a raised temperature, such as a temperature of 50° C. or more, such as a temperature of 60° C. or more, such as a temperature of 70° C. or more, such as a temperature of 80° C. or more, such as a temperature of 90° C. or more.

By increasing the temperature the reaction, such as the dissolution of the inorganic binder precursor particles may be accelerated, whereby the time period for the plurality of scanning procedures may be reduced whereby the determination of determining at least one property associated to a binder quality may be reduces accordingly.

Optionally the pressure may be increased e.g. up to 2 bars, such as up to 1.5 bars where the temperature is relatively high e.g. of 80° C. or more to avoid or reduce undesired evaporation or bubble formation.

In an embodiment, the method comprises correlating dissolution time profile representing the fraction dissolved as a function of time to a reference profile curve based on a previously obtained dissolution time profile representing the fraction dissolved as a function of time obtained an equal condition and a previously obtained compressive strength as a function of curing time curve of a reference inorganic binder obtained from the particulate substance, wherein the previously obtained dissolution time profile representing the fraction dissolved as a function of time obtained an equal condition and a previously obtained compressive strength as a function of curing time curve of the reference inorganic binder obtained from the particulate substance preferably are consolidated.

In an embodiment, the method preferably comprises performing a plurality of runs comprising at least a first and a second run, wherein each run comprises the steps providing a sample mixture comprising a portion of the particulate substance and a portion of the fluid substance,
  performing at least one of scanning procedure, wherein each scanning procedure comprises acquiring at least one light transmission image and/or a light reflection image of an image acquisition area,
  processing the acquired image(s) to obtain at least one processed image of each scanning procedure,
wherein the first run and the second run differs in at least one condition. Preferably the condition comprises at least one of a temperature and an activation fluid. The determination of the at least one binder quality associated property of the particulate substance may be based on the at least one processed image of each scanning procedure of the first run and the at least one processed image of each scanning procedure of the second run.

By performing a plurality of runs at different condition, a desired or even an optimal condition for processing the particulate substance to a partly or fully cured binder may be determined.

The activation fluid may be provided and mixed with the particulate substance to form the sample mixture. Where the particulate substance comprises precursor particle for a geopolymer binder the activation fluid may be provided by including and/or adding activation particles to the particulate substance and adding a liquid, such as water or another aqueous liquid to dissolve at least some of the activation particles to form the fluid substance. Where the particulate substance comprise raw material particles for a non-hydraulic cement binder, the activation fluid may be provided by including and/or adding a liquid, such as water or another aqueous liquid to the particulate substance and thereafter adding carbon dioxide bubbles through the liquid to form the sample mixture comprising the particulate substance and the fluid substance.

The plurality of runs may for example comprise 3 or more runs, such as 4 or more runs, such as 5 or more runs, wherein the plurality runs preferably are performed such that they differs in at least one condition.

In an embodiment, the at least one condition comprises a temperature of the sample mixture, preferably the temperature of the first run differs at least 5° C. from the temperature of the second run, such as differs at least 10° C., such as differs at least 15° C., such as differs at least 20° C.

Thereby the binder quality associated property of the substance may comprise an acceleration factor as a function of temperature which may be determined by comparing the processed image(s) of the scanning procedure(s) of the first run and the processed image(s) of the scanning procedure(s) of the second run.

In an embodiment, the at least one condition comprises type of and/or activator concentration of the activator fluid, such as an activator concentration of the activator fluid, wherein the activator concentration of the activator fluid of the first run differs at least by 0.1 M from the activator concentration of the activator fluid of the second run. Thereby an effective and even optimal activator for the particulate substance may be determined.

In an embodiment, the at least one condition comprises amount of the activator fluid relative to amount of the particulate substance of the sample mixture, wherein the amount of the activator fluid relative to the amount of the particulate substance of the sample mixture of the first run differs at least 1%, such as at least, 2%, such as at least 6%, such as at least 8%, such as at least 10% from the amount of the activator fluid relative to amount of the amount of the particulate substance of the sample mixture of the second run. Thereby an effective and even optimal amount of activator for the particulate substance may be determined.

One or more of the at least one scanning procedure of the first run and one or more of the at least one scanning procedure of the second run may conveniently be performed within a time frame from T1 to T2, wherein T1 is a point in time after T0, where T0 is the time of mixing and wherein T2 is up to 48 hours larger than T1, preferably T2 is from 0.5 minutes to 15 minutes larger than T1.

The scanning procedure(s) of the respective runs may be performed within respective scanning time slots which may be equal or different.

Subsequent scanning procedure(s) may be performed with respective intermediate time slots, which may be equal or different.

Advantageously, the average length of the intermediate time slots are longer than the average length of the scanning time slots, preferably the average length of the intermediate time slots is at least 2 times, such as at least 5 times the average length of the scanning time slots.

Usually the dissolution of the inorganic binder precursor particles starts immediately after the mixture has been established comprising the portion of the particulate substance and a portion of a fluid substance. At the beginning the dissolution is relatively fast where after it may slow down. This can be seen on the dissolution time profile representing the fraction dissolved as a function of time. The lengths of intermediate time slots may advantageously be relatively short at first after the activation has been initiated and lengths of intermediate time slots may increase as the dissolution slows down.

The portion of the particulate substance of the runs may be equal or differ in amount (volume/weight) of particulate substance.

In an embodiment, the portion of the particulate substance of one or more of the runs has been pretreated by a pretreatment process. The pretreatment process may for example comprise at least one of a crushing process, a supplementing process, a sieving process a heat treatment process, preferably the portion of the particulate substance of two or more of the runs have been subjected to pretreatment process that differs from each other.

The supplementing process may comprise supplementing the portion of particulate substance with additional particles. The sieving process may optionally comprising removing a large particle fraction.

In an embodiment, the determination of the at least one binder quality associated property of the substance comprises determining at least one geometric change property, such as a change of particle size, a change of particle size particle size distribution, a change of particle size particle volume, a change of particle size particle volume distribution, a change of particle size particle shape, a change of particle size specific surface area, a change of particle size external surface area and/or a deterioration property, such as a change of roughness, a change revealing cracks and/or a change revealing other defects.

In an embodiment, the processing of the acquired image(s) comprises obtaining a set of images, wherein the set of images comprises at least two different images comprising a same particle of the particulate substance of the sample mixture, preferably the set of images comprises 3 or more different images comprising the same particle of the particulate substance of the sample mixture.

Advantageously, the acquisition of at image of an image acquisition area comprises acquisition of least one light transmission image.

Generally it is desired that the acquisition of at least one light transmission image of an image acquisition area comprises acquisition of plurality of light transmission images of the image acquisition area along a scanning path through the sample mixture, preferably comprising illuminating at least the image acquisition area along the scanning path by emitting light from an illumination device through the sample mixture towards an image acquisition device and acquiring the light transmission images using the image acquisition device.

The scanning process may e.g. be performed as described in found in co-pending patent application DK PA 202370385.

The of plurality of light transmission images of the image acquisition area along a scanning path through the sample mixture may be processed to provide 3D images of at least a number of the inorganic binder precursor particles, such as a plurality of the inorganic binder precursor particles. Advantageously, at least one processed image comprises 3D images of a representative number of the inorganic binder precursor particles, such as at least 5, such as at least 10 such as at least 50, such as at least 100 or even more of the inorganic binder precursor particles.

In an embodiment, the illuminating of the image acquisition area comprises emitting a light beam from the illumination device and towards the image acquisition device, wherein of the light beam passes through the acquisition area to the and wherein the method comprises shaping the light beam to comprise converging bundle of light rays at the acquisition area.

It has been found, that by providing that the light beam to comprise converging bundle of light rays at the acquisition area, the acquired images may reveal more morphological details than where the light beam is not converging.

The converging bundle of light rays may advantageously have a vertex angle of up to 75°, such as from 5° to 65°.

The illumination device comprises comprise one or more light sources, such as a plurality of light sources which are adapted for being independently activated. In an embodiment, the illumination device comprises a RGB LED diode (Light Emission Diode). The may preferably be wavelength adjustable and/or intensity adjustable.

In an embodiment, the acquisition of plurality of light transmission images of the image acquisition area along the scanning path through the sample mixture, comprises translating the image acquisition area stepwise along the scanning path and acquiring the light transmission images between motions of respective steps of the stepwise translations, preferably the lengths of the respective steps are equal or different, more preferably up to 1 cm, such as between 1 μm and 0.5 cm.

The step length may advantageously be selected in dependence of the particulate material that is analyzed and the property or properties that are to be determined.

In an embodiment, the light emitted from the illumination device, comprises light of a light source adapted for emitting monochromatic light or near monochromatic light having a bandwidth if of up to 50 nm, preferably up to 10 nm, such as up, to 5 nm.

The sample mixture may conveniently be provided in a sample support prior to the performing of the at least one scanning procedure.

Advantageously, at least a portion of a sample wall of the sample support, such as a bottom wall and/or a top wall of the sample support, such as the entire sample support is transparent for at least one wavelength of the light emitted from the illumination device through the dispersed sample, Examples of suitable materials for the sample support comprises polymers (e.g. polypropylene, polyethylene terephthalate and polystyrene) and/or glass.

In an embodiment, the sample support is in the form of a sample container, comprising an inlet for feeding the dispersed sample into the sample support and an outlet for outlet of air or a previous dispersed sample. An example of such a suitable sample support is the sample support disclosed in co-pending patent application DK PA 202370385.

In an embodiment, the performing of each of the at least one scanning procedure comprises acquisition of a plurality of light transmission images, preferably comprising comprises for one or more of the particles of the particulate substance, acquiring a set of images comprising at least one image having the particle in focus and at least one image having the particle out of focus, wherein the sets of image preferably comprises at least three images.

In an embodiment, the processing the acquired image(s) to obtain at least one processed image of each scanning procedure comprises processing the acquired light transmission images to synthesizing a 3D image of at least a volume of the particulate substance of the sample mixture.

In an embodiment, the provision of the sample mixture in the sample support comprises mixing at least the portion of the particulate substance in at least the portion of liquid substance and applying the sample mixture in the sample support or applying the portion of the particulate substance and the portion of liquid substance in the sample support and providing that the portion of the particulate substance and the portion of liquid substance are mixed.

In an embodiment, the providing of the sample mixture comprises preparing a mother sample mixture and withdrawing the sample mixture form the mother sample mixture, wherein the preparation of the mother sample mixture comprises mixing a mother portion of the particulate substance with a mother portion of the liquid substance.

BRIEF DESCRIPTION OF THE DRAWINGS

In the following the invention will be further illustrated by the description of a number of illustrative and non-limiting embodiments and examples of the present invention, with reference to the appended drawings.

The figures are schematic and are not drawn to scale and may be simplified for clarity. Throughout, the same reference numerals are used for identical or corresponding parts.

FIG. 5 illustrates a process diagram for performing quality control of produced particulate substance comprising inorganic binder precursor particles for the production of an inorganic binder using an embodiment of the method of the invention, wherein the particulate substance is comprises a mixture of sources.

FIG. 6 illustrates a process diagram for analyzing curing status and/or quality of an at least partly cured binder of a structure, such as a concrete structure using an embodiment of the method of the invention.

DETAILED DESCRIPTION

Figure 1:
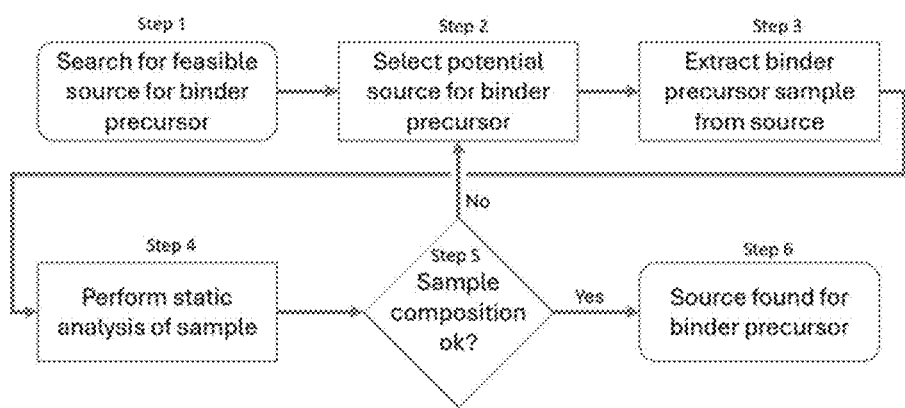
FIG. 1 illustrates a process diagram for determining sources that are suitable for use in the production of particulate substances comprising inorganic binder precursor particles for the production of an inorganic binder using an embodiment of the method of the invention.

The process illustrated in FIG. 1 starts in step 1 by searching for feasible sources for use in the production of an inorganic binder comprising inorganic binder precursor particles. This for example be done by screening the market or looking for suitable locations for mining. In step 2, a potential candidate source for the production of an inorganic binder comprising inorganic binder precursor particles is selected. In step 3, the candidate source is pretreated by extracting particulate substance expected to comprise inorganic binder precursor particles. In step 4, a sample is taken of the pretreated candidate source and one or more static analysis of the sample is performed using at least one embodiment of the invention. The analyses may preferably comprise generating a hyperspectral image as described above to determining the content of the candidate source. In step 5 the analysis results are evaluated.

If the determined content reveal that the candidate source has a too low amount of inorganic binder precursor particles this candidate source is discard and the process return to step 2 for selecting a new candidate source. If the determined content reveal that the analyzed candidate source has sufficient inorganic binder precursor particles to qualify as a source for the production of an inorganic binder, the candidate source is deemed to be an approved source (step 6), and the approved source is classified according to its determined content for optionally being mixed with other sources.

Figure 2:
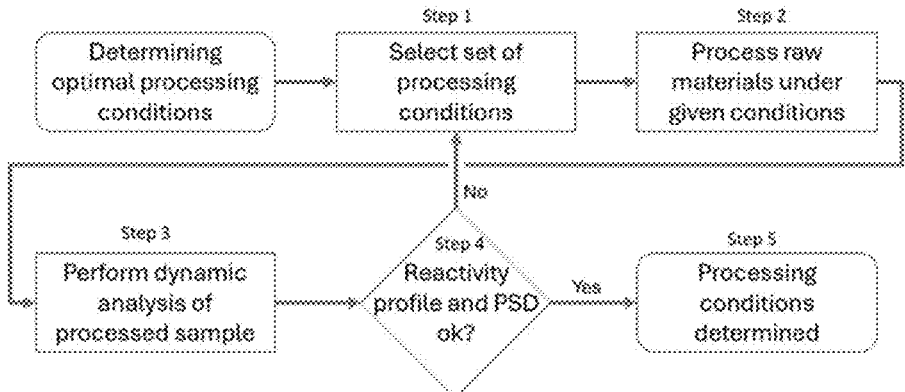
FIG. 2 illustrates a process diagram for determining and optionally optimizing the production of particulate substances comprising inorganic binder precursor particles for the production of an inorganic binder using an embodiment of the method of the invention.

The process illustrated in FIG. 2 starts in step 1 by selecting a set of processing condition, such as processing condition for an approved source e.g. obtained from the process described in FIG. 1. In step 2, a sample of the approved source is obtained and the sample is processed according the set of selected processing conditions. The processing condition may be as described above and e.g. comprising crushing/milling the sample to reduce the sizes of the particles of the particulate substance and/or subjecting the sample to a heat treatment according to the set of conditions. In step 3, one or more static and/or dynamic analysis of the sample is performed using at least one embodiment of the invention. The analyses may preferably comprise performing a particle size determination and/or performing a reactivity determination as described above.

In step 4 the analysis results are evaluated. If the determined content reveal that the particle sizes and/or the determined reactivity are within one or more selected threshold, the set of selected processing conditions is approved (step 5). If not, the process returns to step 1 and select a new set of selected processing conditions.

Figure 3:
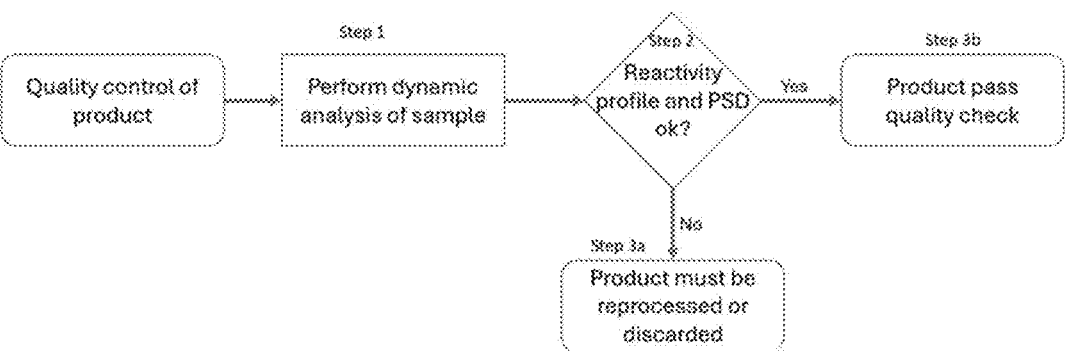
FIG. 3 illustrates a process diagram for performing quality control of produced particulate substances comprising inorganic binder precursor particles for the production of an inorganic binder using an embodiment of the method of the invention.

The process illustrated in FIG. 3 starts in step 1 by taking a sample of produced particulate substances comprising inorganic binder precursor particles for the production of an inorganic binder. The method of production of the produced particulate substances comprising inorganic binder precursor particles for the production of an inorganic binder may e.g. comprise the processing condition determined by the process of FIG. 2.

The sample is subjected to one or more static and/or dynamic analysis, performed using at least one embodiment of the invention. The analyses may preferably comprise performing a particle size determination and/or performing a reactivity determination as described above.

In step 2 the analysis results are evaluated. If the determined content reveal that the particle sizes and/or the determined reactivity are within one or more selected threshold, the quality of the produced particulate substance is approved (step 3*b*). If not, the quality of the produced particulate substance is not approved (step 3*a*) and the produced particulate substance may be sent to reprocessing or be discarded.

Figure 4:
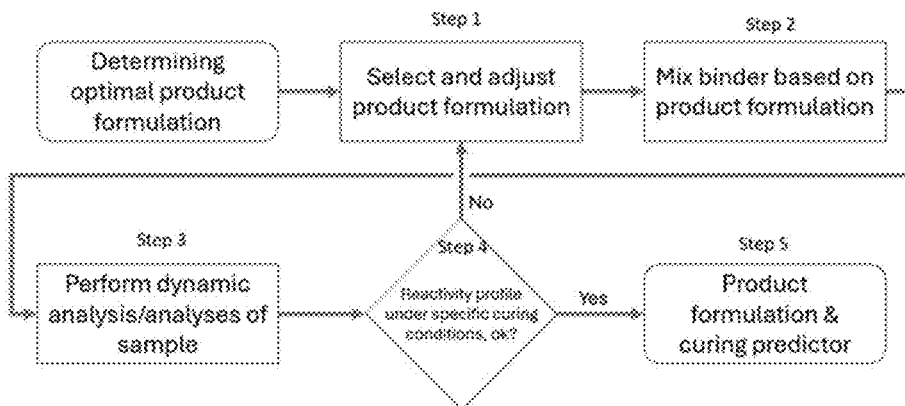
FIG. 4 illustrates a process diagram for determining and optionally optimizing the production of a particulate substance comprising inorganic binder precursor particles for the production of an inorganic binder using an embodiment of the method of the invention, wherein the particulate substance comprises a mixture of sources.

The process illustrated in FIG. 4 starts in step 1 by selecting a candidate product formulation. In step 2, a number of sources according to the candidate formulation are mixed. The sources may comprise approves candidate sources which preferably has been processed according to process conditions determined according to FIG. 2. In step 3, the sample is subjected to one or more static and/or dynamic analysis, performed using at least one embodiment of the invention. The analyses may preferably comprise performing reactivity determination as described above such as reactivity as a function of time e.g. comprising an estimation of setting time and/or compressive strength of a binder obtainable or obtained from the candidate product formulation.

In step 4 the analysis results are evaluated. If the determined content reveal that the determined reactivity are within one or more selected threshold, the formulation is approved (step 5). If not, the process returns to step 1 and a new candidate product formulation is selected.

The process illustrated in FIG. 5 starts in step 1 by extracting a sample from a binder material having a binder formulation preferably determined by the process of FIG. 4. In step 2, the sample is subjected to one or more static and/or dynamic analysis, performed using at least one embodiment of the invention. The analyses may preferably comprise performing reactivity determination as described above such as reactivity as a function of time e.g. comprising an estimation of setting time and/or compressive strength of a binder obtainable or obtained from the candidate product formulation.

In step 3, the analysis results are evaluated. If the determined content reveal that the determined reactivity are within one or more selected threshold, the product pass the quality check (step 4b). If not, the product failed the quality check and may optionally be discarded or it may be mixed with improvement particulate substance and rechecked (step 4a).

The process illustrated in FIG. 5 may conveniently be applied as an on-site product quality test.

The process illustrated in FIG. 6 starts in step 1 by extracting a sample from an at least partly cured binder of a structure, such as a concrete structure. In step 2, the sample is grinded. In step 3, the grinded sample is subjected to one or more static and/or dynamic analysis, performed using at least one embodiment of the invention. The analyses may preferably comprise performing reactivity determination as described above such as reactivity as a function of time e.g. comprising an estimation of setting time and/or compressive strength of a binder obtainable or obtained from the candidate product formulation.

In step 4, the analysis results are evaluated. If the determined content reveal that the determined reactivity are completed to a degree above a selected threshold, the concrete structure is deemed to be fully cured (step 5a). If not, the time to be fully cured is estimated (step 5b).

Figure 7:
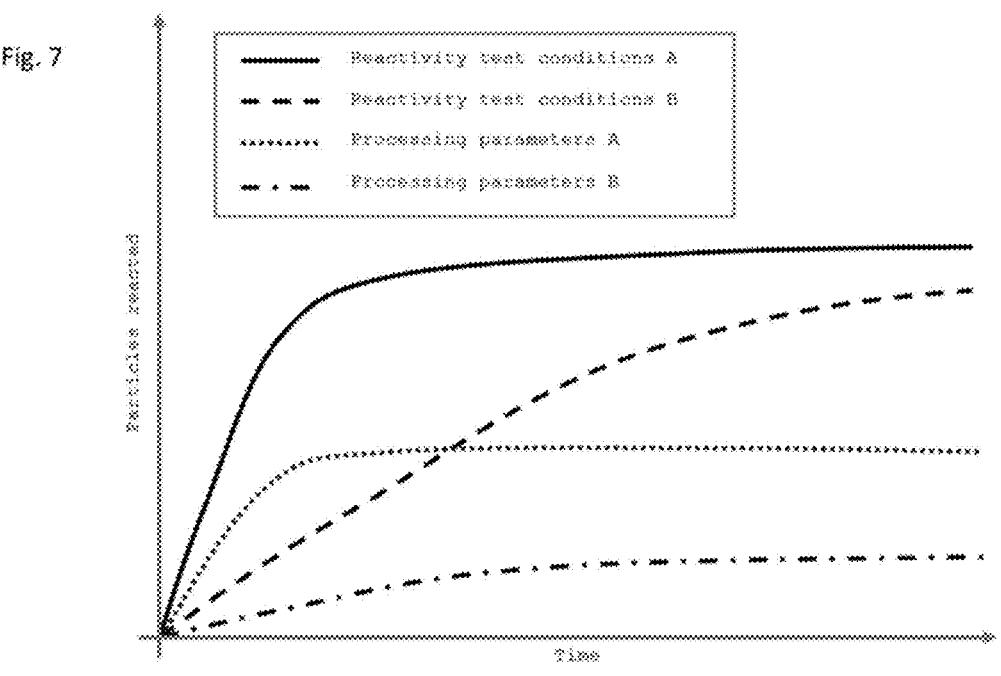
FIG. 7 is a diagram showing reactivity as a function of time of portions of particulate substance at two different test conditions and where the two portions of particulate substance have been processed using different processing parameters

The reactivity as a function of time shown in FIG. 7 comprises reactivity as a function of time of a particulate substance comprising inorganic binder precursor particles for a hydraulic cement where the reactivity test is performed at a first set of conditions A and a second set of conditions B. The set of conditions may be as described above.

The reactivity as a function of time shown in FIG. 7 also comprises reactivity as a function of time of a particulate substance comprising inorganic binder precursor particles for a hydraulic cement where the inorganic binder precursor particles has been subjected to a first set of processing parameters A and a second set of processing parameters B. The set of processing parameters may be as described above.

Figure 8:
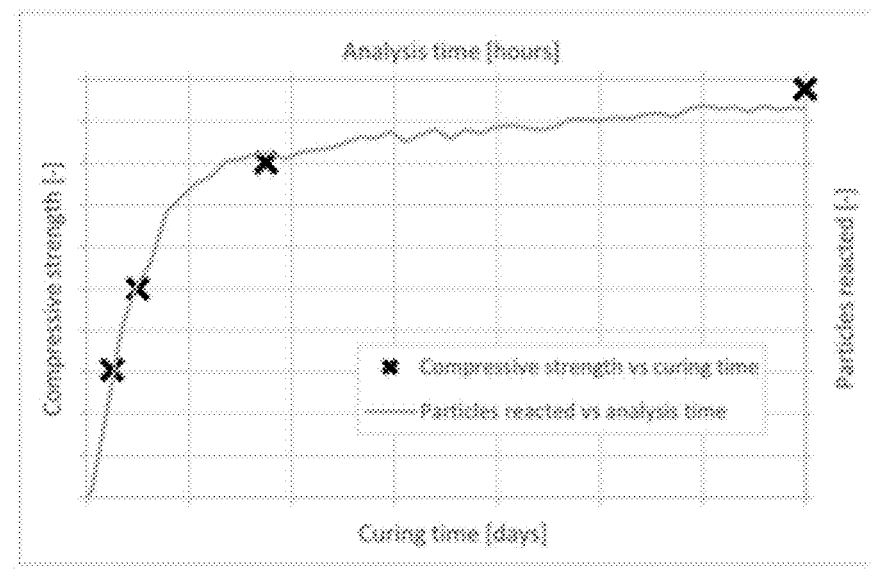
FIG. 8 is a diagram showing a dissolution time profile representing the fraction dissolved material as a function of time of calcined inorganic binder precursor particles suitable for a hydraulic cement.
Figure 9:
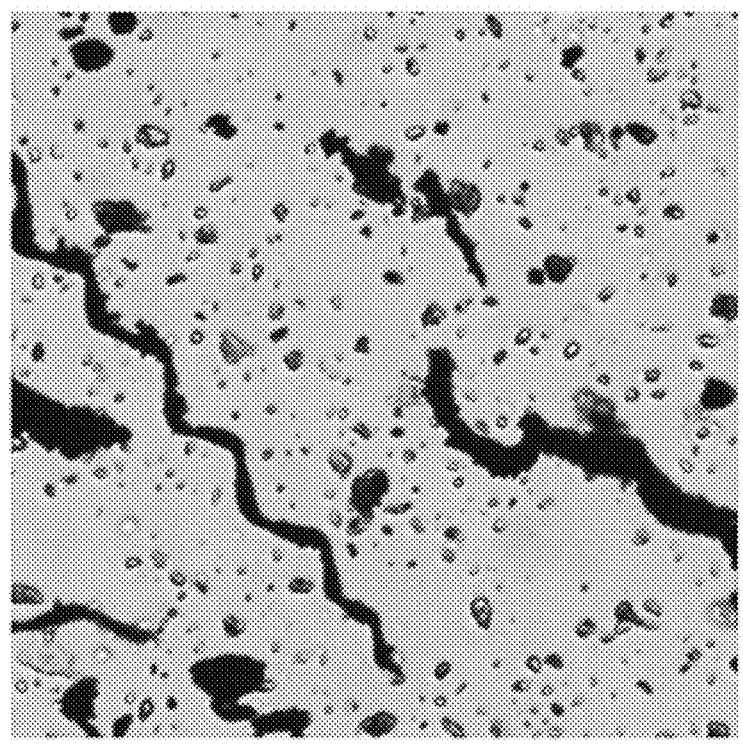
FIG. 9 shows a processed image of a sample mixture comprising a portion of particulate substance comprising inorganic binder precursor particles for a geopolymer and water.

In the diagram of FIG. 8 a dissolution time profile representing the fraction dissolved material of particulate substance for hydraulic cement as a function of time determined according to the method as described above over the analysis time. The dissolution time profile is correlate to measurements of compressive strength of a cement of the same particulate substance for hydraulic cement during curing and it can be seen that there is a very high correlation there between which shows that the dissolution time profile of a particulate substance comprising inorganic binder precursor particles may be used to estimate the obtainable compressive strength.

The processed image shows that the different characteristics of the particles, such as sized, shapes and colors may be determined with a very high accuracy.

Figure 10A:
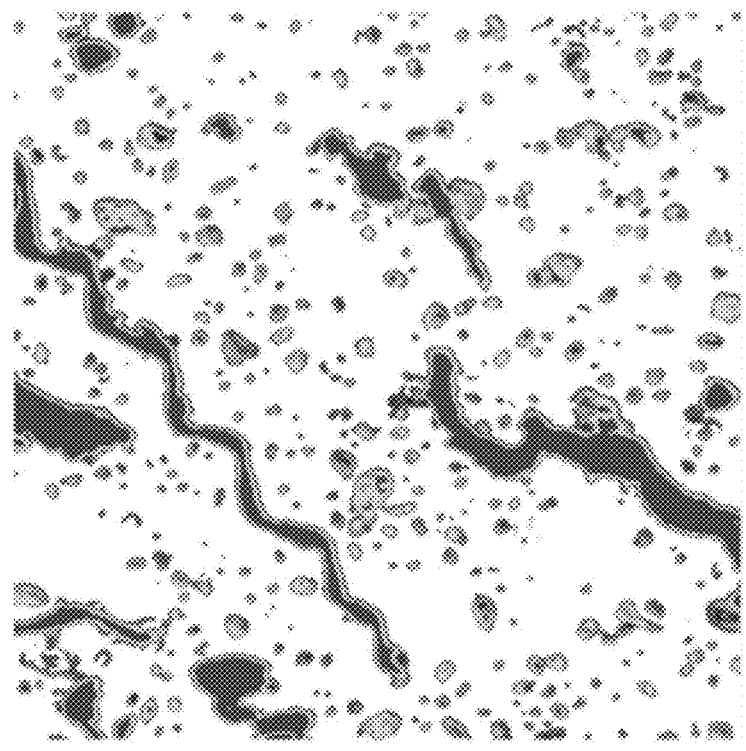
FIGS. 10*a* and 10*b* in respectively color and black/gray/ white shows a processed image of the sample mixture shown in FIG. 9, wherein the processed image is a hyperspectral image obtained from several processed images.
Figure 10B:
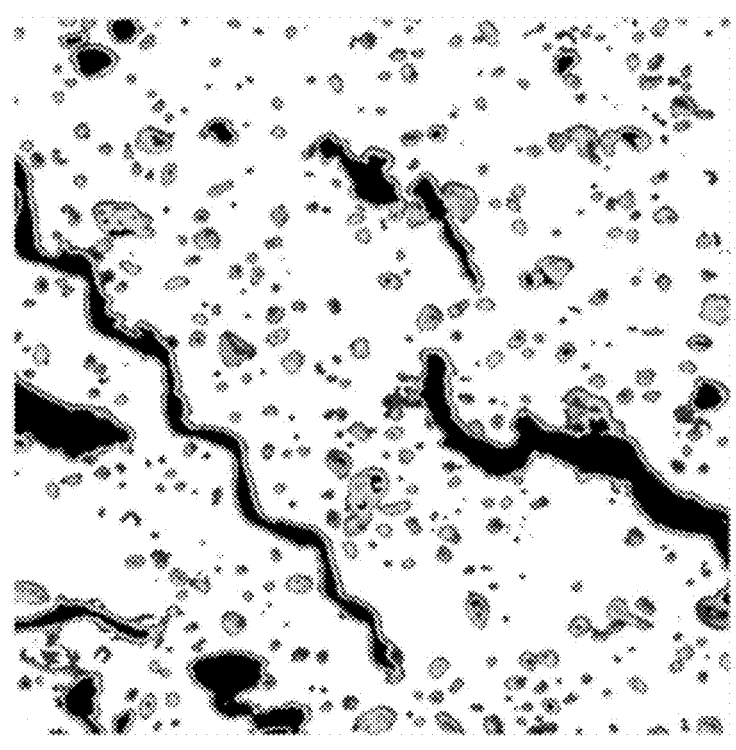

The hyperspectral image shown I FIGS. 10a and 10b show very clearly reveal the different contents of the particle of the particulate substance and thereby shows that the contents and the respective amounts may be determined as described above based on one or more hyperspectral images.

Figure 11:
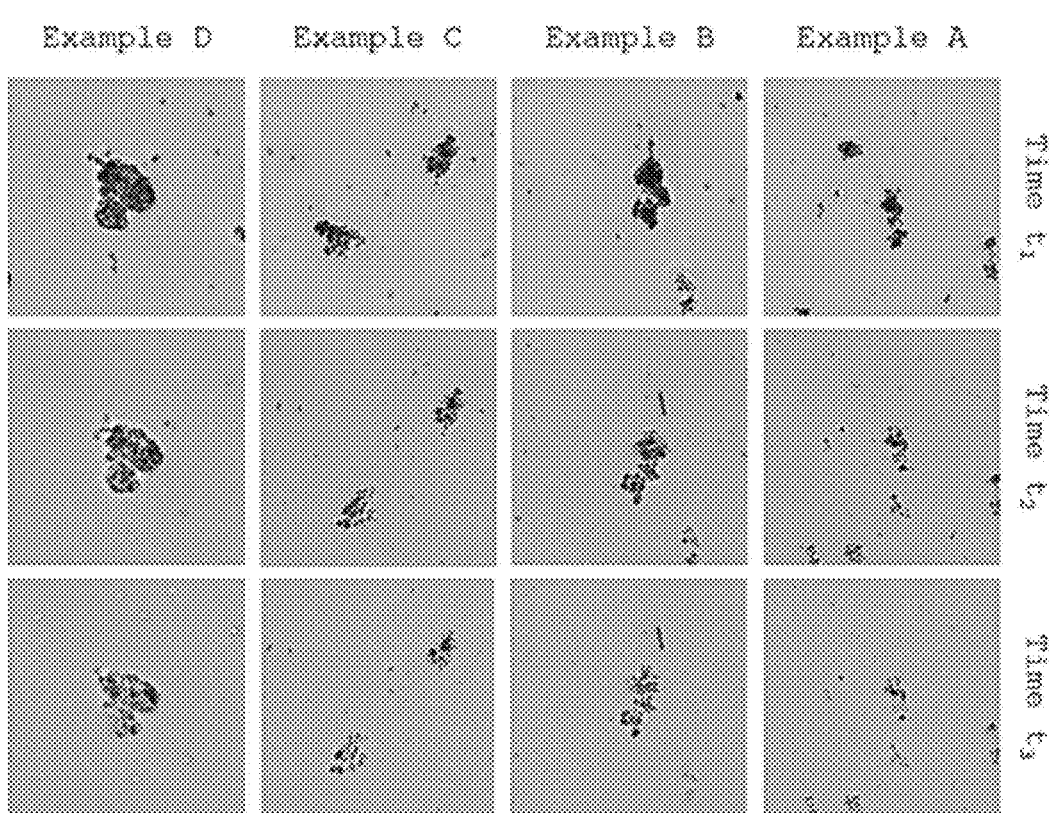
FIG. 11 shows dissolution over time of inorganic binder precursor particles for respectively a geopolymeric binder and a hydraulic cement binder.

FIG. 11 shows dissolution over time of four different samples A, B, C, D of inorganic binder precursor particles.

Sample A and B are hydraulic cement precursor particles and sample B and C are geopolymer precursor particles.

For all the sample it can be seen that at the time $t_1$, only a miner portion of the particles are dissolved. At the time $t_2$, a larger portion of the particles are dissolved and at the time $t_3$, a much larger portion of the particles are dissolved.

The invention claimed is:

1. A method of examining a particulate substance comprising inorganic binder precursor particles, wherein the examination comprises determining at least one property associated to a binder quality of the particulate substance comprising:

providing a sample mixture comprising a portion of the particulate substance and a portion of a liquid substance, performing at least one scanning procedure, wherein each scanning procedure comprises acquiring at least one image of an image acquisition area, processing the acquired image(s) to obtain at least one processed image of each scanning procedure, and determining said at least one binder quality associated property of at least the portion of the particulate substance, wherein the performing of the at least one scanning procedure comprises performing a plurality of scanning procedures, over an activation time period and for each scanning procedure obtaining at least one processed image, wherein the processed image(s) for each scanning procedures comprises a set of absorbance data and is associated to a time attribute representing the time of performing the scanning procedure, wherein the portion of liquid substance comprises an activator liquid and wherein the determination of said at least one binder quality associated property of the particulate substance comprises determining quantitatively fraction dissolved of a at least a selected group of particles of the scanned sample mixture of the particulate over at least a part of the activation time period and preparing a dissolution time profile representing the fraction dissolved as a function of time.

2. A method of claim 1, wherein the inorganic binder precursor particles comprises fresh inorganic binder precursor particles for production of a fresh binder and/or particles of a crushed structure comprising residual inorganic binder precursor particles.

3. The method of claim 1, wherein the determining of at least one binder quality associated property of the particulate substance comprises determining if a portion of residual inorganic binder precursor particles comprises uncured precursor particles and wherein the at least one binder quality associated property comprises a quantitative and/or a qualitative determination of uncured inorganic binder precursor particles.

4. The method of claim 1, wherein the step of providing the sample mixture comprises obtaining the portion of the inorganic binder precursor particles and mixing the obtained portion of inorganic binder precursor particles with the portion of the liquid substance to provide the sample mixture to comprise at least 90%, by weight of the liquid substance.

5. The method of claim 1, wherein the inorganic binder precursor particles comprises:
   i. inorganic binder precursor particles in the form of geopolymeric particles comprising precursor particle for a geopolymer binder;
   ii. inorganic binder precursor particles in the form of raw material particles for a hydraulic cement binder comprising un-calcined hydraulic cement precursor particles;
   iii. inorganic binder precursor particles in the form of fully or partially calcined materials for a hydraulic cement binder;
   iv. inorganic binder precursor particles in the form of raw material particles for a non-hydraulic cement binder; or
   v. any mixtures comprising one or more of the above mentioned i-iv.

6. The method of claim 1, wherein binder quality associated property comprises a static property, and wherein the method comprises selecting the portion of the liquid substance to be non-reactive and/or non-dissolving of at least the inorganic binder precursor particles and/or activator particles of the particulate substance.

7. The method of claim 1, wherein binder quality associated property comprises a change property and wherein the method comprises selecting the portion of the liquid substance to comprise an activator liquid.

8. The method of claim 1, wherein the inorganic binder precursor particles comprises inorganic binder precursor particles in the form of geopolymeric particles and wherein the binder quality associated property comprises a geopolymerization associated property and wherein the geopolymeric particles comprises a source of alumina and a source of silicate.

9. The method of claim 8, wherein the particulate substance comprises support particles, wherein the support particles are at least partly dissolvable in the portion of liquid substance and wherein the at least one property associated to a geopolymerization reactivity of the substance determined comprises a determination of one or more parameters associated to the solvability of the support particle and wherein the support particle comprises activator particles.

10. The method of claim 8, wherein the portion of liquid substance comprising an alkaline activator liquid or an acidic activator liquid, selected from the group comprising a solution comprising one or more of Sodium Hydroxide (NaOH), Potassium Hydroxide (KOH), alkali metal oxide Silicate (Water Glass), Sodium Carbonate (Soda Ash), Potassium Carbonate (K2CO3).

11. The method of claim 1, wherein the inorganic binder precursor particles comprises inorganic binder precursor particles in the form of raw material particles for a hydraulic cement binder comprising un-calcined, partially calcined or fully calcined hydraulic cement precursor particles, and wherein the binder quality associated property comprises a cement quality associated property.

12. The method of claim 1, wherein the inorganic binder precursor particles comprises or consists of inorganic binder precursor particles in the form of fully or partially calcined material particles for a hydraulic cement binder.

13. The method of claim 1, wherein the inorganic binder precursor particles comprises or consists of inorganic binder precursor particles in the form of raw material particles for a non-hydraulic cement binder and wherein the binder quality associated property comprises a non-hydraulic cement quality associated property.

14. A method of examining a particulate substance comprising inorganic binder precursor particles, wherein the examination comprises determining at least one property associated to a binder quality of the particulate substance comprising:
   providing a sample mixture comprising a portion of the particulate substance and a portion of a liquid substance,
   performing at least one scanning procedure, wherein each scanning procedure comprises acquiring at least one image of an image acquisition area,
   processing the acquired image(s) to obtain at least one processed image of each scanning procedure, and
   determining said at least one binder quality associated property of at least the portion of the particulate substance,
   wherein the performing of the at least one scanning procedure comprises performing a set of scanning procedures comprising at least two scanning procedures, each scanning procedure of the set of scanning procedures comprises illuminating at least said image acquisition area of said sample mixture by a light source, wherein the light source differs in wavelength from a first of the two scanning procedures to another of the at least two scanning procedures, wherein the at least one processed image of each scanning procedure of the set of scanning procedures comprises absorbance data and wherein method further comprises combining the absorbance data for two or more of the processed image to provide a hyperspectral image and wherein the determining of said at least one binder quality associated property of at least the portion of the particulate substance is based on the hyperspectral image.

15. The method of claim 14, wherein the determination of said at least one binder quality associated property of the particulate substance comprises determining at least one content property comprising determining qualitatively and/or quantitatively at least one chemical component selected from the group comprising alumina moieties, silicate moieties, silica (SiO2), alumina (Al2O3), dicalcium silicate (C2S), tricalcium aluminate (3A), tetracalcium aluminoferrite (C4AF), tricalcium silicate (C3S), dicalcium silicate (C2S) and/or tricalcium aluminate (C3A), tetracalcium aluminoferrite (C4AF).

16. The method of claim 14, wherein the method comprises obtaining a plurality of the hyperspectral images over a time period, wherein each hyperspectral images is associated to a time attribute, wherein the portion of liquid substance comprises an activator liquid and wherein the determination of said at least one binder quality associated property of the particulate substance comprises determining at least one content change property, at least one geometric change property and/or at least one deterioration property based on one or more differences of absorbance data between two or more of the hyperspectral images obtained over the time period and associated to different time attributes.

17. The method of claim 1, wherein the method further comprises estimating a strength parameter of an at least partly cured binder obtained or obtainable from the particulate substance, wherein the estimation is based on the dissolution time profile representing the fraction dissolved as a function of time, wherein the strength parameter is selected from compressive strength, tensile strength, flexural strength, shear strength, bond strength and/or durability-related strengths.

18. A method of examining a particulate substance comprising inorganic binder precursor particles, wherein the examination comprises determining at least one property associated to a binder quality of the particulate substance comprising:

providing a sample mixture comprising a portion of the particulate substance and a portion of a liquid substance, performing at least one scanning procedure, wherein each scanning procedure comprises acquiring at least one image of an image acquisition area, processing the acquired image(s) to obtain at least one processed image of each scanning procedure, and determining said at least one binder quality associated property of at least the portion of the particulate substance, wherein the method comprises at least one of estimating a compressive strength of a fully cured binder obtained or obtainable from the particulate substance, wherein a dissolution time profile representing the fraction dissolved as a function of time comprises a plateau and wherein the estimation is based on the plateau of the dissolution time profile representing a fraction dissolved as a function of time;

estimating a curing time at a selected curing condition to reach a selected compressive strength of an inorganic binder obtained or obtainable from the particulate substance; and/or estimating a compressive strength of a partially cured binder obtained or obtainable from the particulate substance, wherein the dissolution time profile representing the fraction dissolved as a function of time comprises a progression phase, wherein the estimation is based on the progression phase of the dissolution time profile representing the fraction dissolved as a function of time.

19. A method of examining a particulate substance comprising inorganic binder precursor particles, wherein the examination comprises determining at least one property associated to a binder quality of the particulate substance comprising:

providing a sample mixture comprising a portion of the particulate substance and a portion of a liquid substance, performing at least one scanning procedure, wherein each scanning procedure comprises acquiring at least one image of an image acquisition area, processing the acquired image(s) to obtain at least one processed image of each scanning procedure, and determining said at least one binder quality associated property of at least the portion of the particulate substance, wherein the method comprises performing a plurality of runs comprising at least a first and a second run, wherein each run comprises the steps:

providing a sample mixture comprising a portion of the particulate substance and a portion of the liquid substance, performing at least one scanning procedure, wherein each scanning procedure comprises acquiring at least one light transmission image and/or a light reflection image of an image acquisition area, processing the acquired image(s) to obtain at least one processed image of each scanning procedure, wherein the said first run and said second run differs in at least one condition, wherein the condition comprises at least one of a temperature and an activation liquid wherein the determination of said at least one binder quality associated property of the particulate substance is based on said at least one processed image of each scanning procedure of the first run and said at least one processed image of each scanning procedure of the second run.

20. The method of claim 1, wherein the method comprises providing that said sample mixture is provided in a sample support prior to the performing of said at least one scanning procedure, wherein at least a portion of a sample wall of said sample support is transparent for at least one wavelength of the light emitted from the illumination device through said sample mixture and wherein the sample support is in the form of a sample container, comprising an inlet for feeding the sample mixture into the sample support and an outlet for outlet of air or a previous sample mixture.

21. The method of claim 1, wherein at least one of the plurality of light transmission images is acquired through a polarized filter.

22. A method of examining a particulate substance comprising inorganic binder precursor particles, wherein the examination comprises determining at least one property associated to a binder quality of the particulate substance comprising:

providing a sample mixture comprising a portion of the particulate substance and a portion of a liquid substance, performing at least one scanning procedure, wherein each scanning procedure comprises acquiring a plurality of light transmission images of an image acquisition area along a scanning path through the sample mixture, processing the acquired images to obtain at least one processed image of each scanning procedure, and determining said at least one binder quality associated property of at least the portion of the particulate substance, wherein the processing the acquired images to obtain at least one processed image of each scanning procedure comprises processing the acquired light transmission images to synthesizing a 3D image of at least a volume of the particulate substance of the sample mixture, and wherein the determining said at least one binder quality associated property of at least the portion of the particulate substance is performed based on said at least one synthesized 3D image.

\* \* \* \* \*